(12) United States Patent
Nakada et al.

(10) Patent No.: US 12,089,879 B2
(45) Date of Patent: Sep. 17, 2024

(54) INTERNAL FIXATION MEMBER SET AND INTERNAL FIXATION MEMBER

(71) Applicant: KYOCERA CORPORATION, Kyoto (JP)

(72) Inventors: Fumiya Nakada, Osaka (JP); Kazuhiro Nagai, Yasu (JP)

(73) Assignee: KYOCERA CORPORATION, Kyoto (JP)

( * ) Notice: Subject to any disclaimer, the term of this patent is extended or adjusted under 35 U.S.C. 154(b) by 210 days.

(21) Appl. No.: 17/777,523

(22) PCT Filed: Nov. 25, 2020

(86) PCT No.: PCT/JP2020/043732
§ 371 (c)(1),
(2) Date: May 17, 2022

(87) PCT Pub. No.: WO2021/106900
PCT Pub. Date: Jun. 3, 2021

(65) Prior Publication Data
US 2022/0395297 A1    Dec. 15, 2022

(30) Foreign Application Priority Data
Nov. 29, 2019  (JP) ................................. 2019-216768

(51) Int. Cl.
*A61B 17/70*    (2006.01)
(52) U.S. Cl.
CPC ...... *A61B 17/7037* (2013.01); *A61B 17/7032* (2013.01)

(58) Field of Classification Search
CPC ............ A61B 17/7032; A61B 17/7035; A61B 17/7037–7038; A61B 17/7055
See application file for complete search history.

(56) References Cited

U.S. PATENT DOCUMENTS

| 7,691,131 B2 | 4/2010 | Graf | |
|---|---|---|---|
| 2008/0177322 A1* | 7/2008 | Davis | A61B 17/7037 606/266 |
| 2015/0112390 A1* | 4/2015 | Fang | A61B 17/7037 606/279 |
| 2018/0021068 A1* | 1/2018 | May | A61B 17/7038 606/266 |
| 2019/0029731 A1* | 1/2019 | Shoshtaev | A61B 17/861 |

* cited by examiner

*Primary Examiner* — Eduardo C Robert
*Assistant Examiner* — Michelle C Eckman
(74) *Attorney, Agent, or Firm* — Procopio, Cory, Hargreaves & Savitch LLP

(57) ABSTRACT

An internal fixation member set includes an internal fixation member, an inner member, and an outer member. The outer member has a first opening and a second opening, and rotatably retains a head of the inner fixation member. The inner member is inside the outer member and movable between a first position farther from the head and a second position nearer the second opening than the first position. The head has a first rotation range with the inner member at the first position and a second rotation range with the inner member at the second position. The second rotation range is smaller than the first rotation range with an interference between interference parts. A reference rotational position at which the head is insertable into or extractable from the outer member is included in the first rotation range and is not included in the second rotation range.

14 Claims, 22 Drawing Sheets

INTERNAL FIXATION MEMBER SET AND INTERNAL FIXATION MEMBER

CROSS-REFERENCE TO RELATED APPLICATION

The present application is a National Phase entry based on PCT Application No. PCT/JP2020/043732 filed on Nov. 25, 2020, entitled "INTERNAL FIXATION MEMBER SET AND INTERNAL FIXATION MEMBER", which claims the benefit of Japanese Patent Application No. 2019-216768, filed on Nov. 29, 2019, entitled "INTERNAL FIXATION MEMBER SET AND INTERNAL FIXATION MEMBER". The contents of which are incorporated by reference herein in their entirety.

FIELD

Embodiments of the present disclosure relate generally to an internal fixation member set and an internal fixation member.

BACKGROUND

Intervertebral connection devices are known in orthopedics. An intervertebral connection device includes a movable element, an intermediate element, a fixation element, and an anti-falling screw. The intermediate element is fitted in the movable element in a rotatable manner. The fixation element is a screw to be secured to a vertebra and has a head fitted in the intermediate element in a rotatable manner. The anti-falling screw is, outside the movable element, detachably screwed into the fixation element and prevents the fixation element from falling off the intermediate element.

SUMMARY

An internal fixation member set and an internal fixation member are described. In one embodiment, the internal fixation member set includes an internal fixation member, an outer member, and an inner member. The internal fixation member includes an internal fixation member body and a head located on an end of the internal fixation member body. The outer member has a first opening and a second opening, and rotatably retains the head. The inner member is inside the outer member and nearer the first opening than the head. The inner member is movable between a first position farther from the head and a second position nearer the second opening than the first position. The inner member includes a first interference part that interferes with the head. The head includes a second interference part that interferes with the first interference part of the inner member. The head has a first rotation range with the inner member at the first position and a second rotation range with the inner member at the second position. The second rotation range is smaller than the first rotation range with an interference between the first interference part and the second interference part. The head has a reference rotational position at which the head is insertable into or extractable from the outer member. The reference rotational position is included in the first rotation range and is not included in the second rotation range.

In one embodiment, the internal fixation member is retainable by an outer member being tubular and having a first opening and a second opening and by an inner member movable between a first position and a second position inside the outer member. The internal fixation member includes an internal fixation member body and a head. The internal fixation member body is placeable in a bone. The head is joined to one end of the internal fixation member body. The head is retainable nearer the second opening than the inner member inside the outer member. The inner member includes a first interference part that interferes with the head. The head includes a second interference part that interferes with the first interference part of the inner member. The head has a first rotation range with the inner member at the first position and a second rotation range with the inner member at the second position. The second rotation range is smaller than the first rotation range with an interference between the first interference part and the second interference part. The first rotation range includes a reference rotational position, and the second rotation range does not include the reference rotational position.

DETAILED DESCRIPTION

An internal fixation member set for a bone and an internal fixation member according to one or more embodiments of the present disclosure will now be described. The internal fixation member set includes elements that are assembled with a simple operation and are less likely to be separable from one another.

Figure 1:
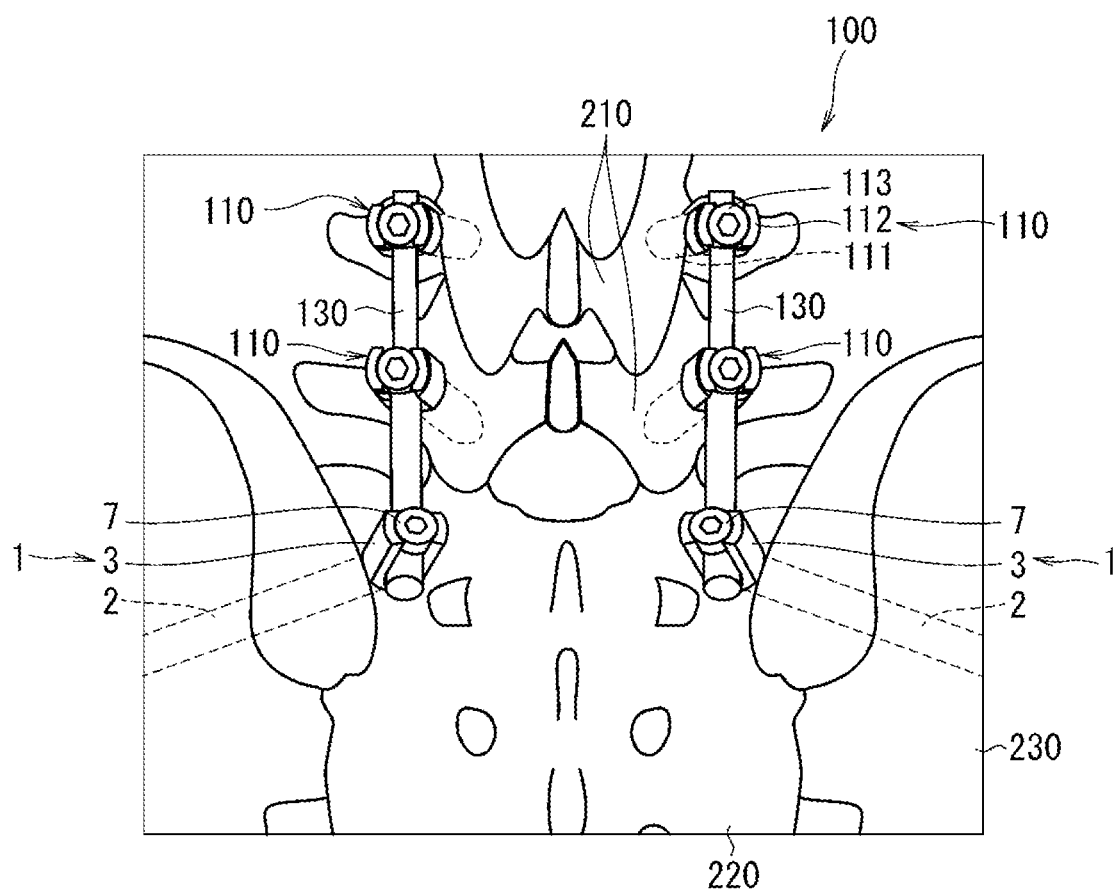
FIG. 1 illustrates a schematic diagram of an example biocompatible implant.

In the example described below, the body of the internal fixation member is a screw. FIG. 1 is a schematic diagram of an example biocompatible implant 100. In the example of FIG. 1, the implant 100 is a human spinal implant. The implant 100 fixes lumbar vertebrae 210, a sacrum 220, and an ilium 230 to one another in the body.

The implant 100 includes screw assemblies 110, screw assemblies 1, and rods 130. These components are formed from biocompatible materials. The materials include, for example, at least one selected from the group consisting of titanium, a titanium alloy, a cobalt-chromium alloy, and stainless steel.

In the example of FIG. 1, the screw assemblies 110 are embedded in the right and left parts of the lumbar vertebrae 210, and the screw assemblies 1 are embedded in the right and left parts of the sacrum 220. In the example of FIG. 1, the screw assemblies 1 are inserted through the sacral alae of the second sacral vertebra of the sacrum 220, penetrate the sacroiliac, and are embedded in the ilium 230 immediately above the greater sciatic notch.

In the example of FIG. 1, the screw assemblies 110 and the screw assembly 1 on the right are interconnected with one rod 130. The rod 130 is cylindrical. The screw assemblies 110 and the screw assembly 1 on the left are interconnected with another rod 130.

Each screw assembly 110 includes a screw 111, a connector 112, and a fastener 113. The connector 112 is tubular, and the head of the screw 111 is placed in the tube. The screw 111 extends outward from the connector 112 and is embedded in the corresponding lumbar vertebra 210. The head of the screw 111 is rotatable with respect to the connector 112. This allows the posture of the connector 112 to be adjusted with the screw 111 embedded in the lumbar vertebra 210.

The connector 112 receives a portion of the rod 130 in the longitudinal direction and laterally holds the received portion of the rod 130 in the longitudinal direction. The posture of the connector 112 is adjusted to receive the rod 130 with the screw 111 embedded in the lumbar vertebra 210. The fastener 113 is, for example, a bolt and is tightened onto the connector 112. The tightening fixes the rod 130 in the connector 112.

Each screw assembly 1, similarly to the screw assembly 110, includes a screw 2, a connector 3, and a fastener 7. The connector 3 is tubular, and the head 22 of the screw 2 is rotatably placed in the tube. The screw 2 extends outward from the connector 3. The screw 2 is embedded in the sacrum 220 and the ilium 230. The sacrum 220 and the ilium 230 will also be collectively referred to as a target bone. The head 22 of the screw 2 is rotatable with respect to the connector 3, allowing the posture of the connector 3 to be adjusted with the screw 2 embedded in the target bone.

The connector 3 receives a portion of the rod 130 in the longitudinal direction and laterally holds the received portion of the rod 130 in the longitudinal direction. The posture of the connector 3 is adjusted to receive the rod 130 with the screw 2 embedded in the target bone. The fastener 7 is, for example, a bolt tightened onto the connector 3 to fix the rod 130.

In the implant 100, the screw assembly 110 is embedded in the lumbar vertebra 210, and the screw assembly 1 is embedded in the sacrum 220 and the ilium 230. The screw assembly 110 and the screw assembly 1 are interconnected with the rod 130. This fixes the lumbar vertebra 210, the sacrum 220, and the ilium 230 to one another.

The ilium 230 is lateral to the sacrum 220, and thus the screw 2 extends laterally. For example, the screw 2 of the right screw assembly 1 extends rightward, whereas the screw 2 of the left screw assembly 1 extends leftward. More specifically, unlike the screw assembly 110, the rotation range of the screw 2 with respect to the connector 3 may not be isotropic, but may be broader in one direction lateral to the connector 3.

Figure 2:
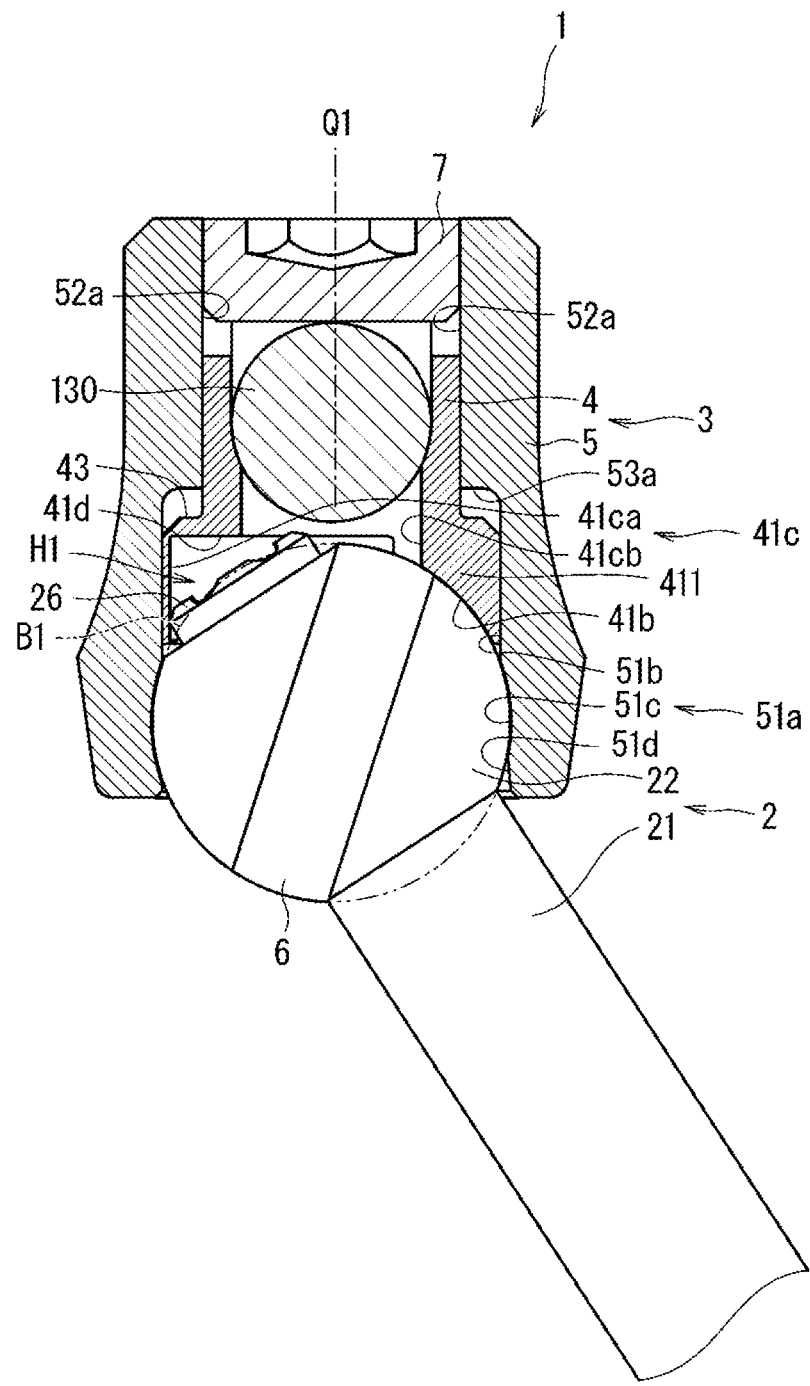
FIG. 2 illustrates a schematic cross-sectional view of an example screw assembly.
Figure 3:
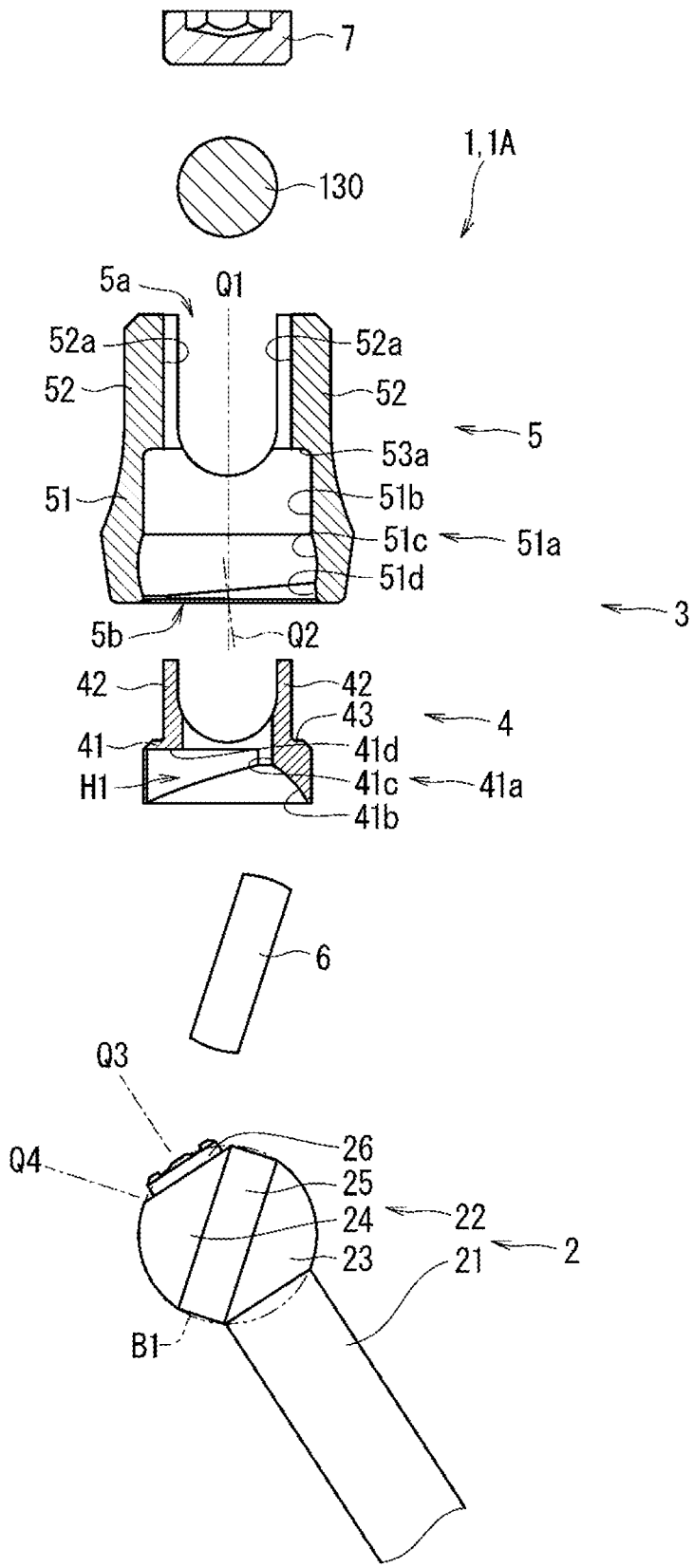
FIG. 3 illustrates an exploded schematic cross-sectional view of the screw assembly.
Figure 4:
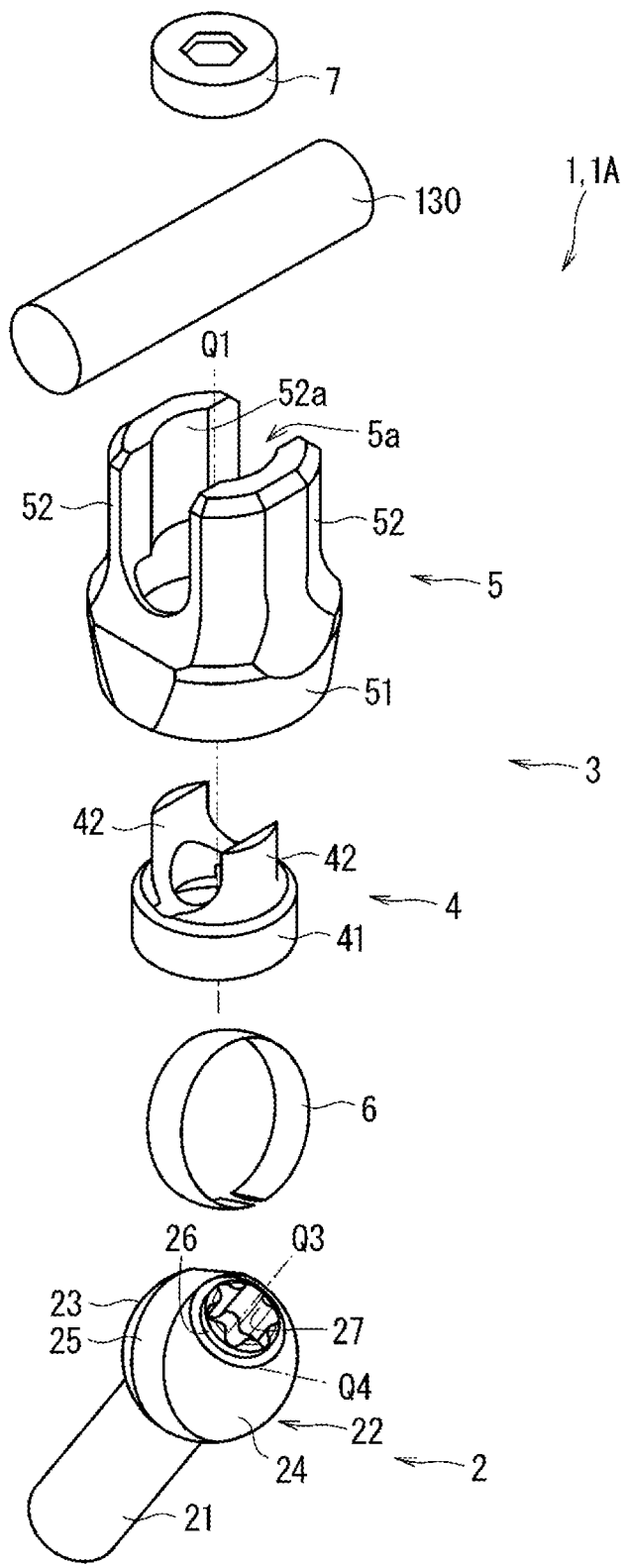
FIG. 4 illustrates an exploded schematic perspective view of the screw assembly.

An example of the screw assembly 1 will now be described in detail. FIG. 2 is a schematic cross-sectional view of an example of the screw assembly 1. FIG. 3 is an exploded schematic cross-sectional view of the screw assembly 1. FIG. 4 is an exploded schematic perspective view of the screw assembly 1.

The screw assembly 1 includes the screw 2, which is an example internal fixation member, the connector 3, and the fastener 7. The screw 2 is a component to be embedded in the target bone. The connector 3 is a component for connecting the screw 2 and the rod 130, and includes an inner member 4 and an outer member 5. The screw assembly 1 includes the screw 2, the inner member 4, the outer member 5, and the fastener 7 as components, and is constructed by assembling these components. The set of these components yet to be assembled is also referred to as a screw set 1A (internal fixation member set). FIGS. 3 and 4, in which the components are separated, can also be views of the screw set 1A. Each component will be outlined first, and then described in detail.

The screw 2 includes the head 22 and a screw body 21, which is an example internal fixation member body. The screw body 21 is elongated. The screw body 21 is embedded from its distal end into the target bone. The head 22 is substantially spherical and connected to the other end (also referred to as the proximal end) of the screw body 21.

The outer member 5 has a substantially tubular shape with a first opening 5a and a second opening 5b. More specifically, the outer member 5 has a substantially cylindrical shape having a central axis Q1. The outer member 5 rotatably retains the head 22 of the screw 2. The outer member 5 has, in its inner peripheral surface, a spherical concave surface 51c conforming to an imaginary spherical surface B1 of the head 22, and the head 22 is fitted in the spherical concave surface 51c. Although the head 22 is, as described later, fixed inside the outer member 5 with the fastener 7, the head 22 is rotatable inside the outer member 5 at least before tightening. The outer member 5 may be formed from a cobalt-chromium alloy, which has high strength.

The positional relationship between the components will be described. The part with the second opening 5b will be referred to as a lower side, whereas the part with the first opening 5a will be referred to as an upper side. The upper and lower sides are unrelated to a vertical direction and defined in accordance with the shape of the outer member 5. In the example below, the second opening 5b will also be referred to as a lower opening 5b, and the first opening 5a will also be referred to as an upper opening 5a.

The screw body 21 of the screw 2 is below the outer member 5 and extends from the head 22 outside the outer member 5. The rotatability of the head 22 with respect to the outer member 5 allows the screw 2 to swing about the head 22 with respect to the connector 3. The swing refers to the movement of the distal end of the screw body 21 about the head 22 along the imaginary spherical surface. In other words, the screw body 21 has variable inclination angles with respect to the outer member 5.

The inner member 4 fits inside the outer member 5 and is above the head 22. The inner member 4 presses the head 22 downward with the fastener 7 as described later. The press holds the head 22 between the inner member 4 and the lower part of the spherical concave surface 51c. This fixes the rotational position of the head 22. The inner member 4 is in contact with an interference part 26 (described later) on the head 22 to restrict the rotation range of the head 22. This will be described in detail later.

The outer member 5 receives a portion of the rod 130 in the longitudinal direction through the upper opening 5a. The fastener 7 is inserted into the upper opening 5a of the outer member 5. The fastener 7 is, for example, a bolt such as a hexagon socket bolt and is screwed into the inner peripheral surface of the upper end of the outer member 5. The distal end of the fastener 7 is placed into contact with the rod 130 to press the rod 130 downward. In response to the press, the rod 130 presses the inner member 4 downward, and the inner member 4 presses the head 22 downward. In this manner, the rod 130 and the head 22 are fixed inside the outer member 5.

Examples of the components described above will now be described in more detail.

In the illustrated example, the screw body 21 has a substantially cylindrical shape with a central axis Q3 and has a thread (not shown) on its outer peripheral surface. The thread spirals from the distal end of the screw body 21 toward the other end. The screw body 21 is embedded in the target bone as described above. The screw 2 to be embedded in the sacrum 220 and the ilium 230 is also referred to as an S2AI screw. The screw body 21 is also referred to as the shaft of the screw 2.

The head 22 is connected to one end of the screw body 21. The screw body 21 and the head 22 may be formed from the same material and integrated together. The head 22 is substantially spherical. The head 22 is located on the central axis Q3, and more specifically, the center of the head 22 may be located on the central axis Q3.

Referring to FIG. 3, the head 22 includes a pair of semispherical parts 23 and 24, a flat belt 25, and the interference part 26. The pair of semispherical parts 23 and 24 have a shape conforming to the imaginary spherical surface B1. In the illustrated example, the imaginary spherical surface B1 has a greater diameter than the screw body 21. The semispherical part 23 is joined to one end of the screw body 21.

The flat belt 25 is a belt-shaped flat surface along the full circumference of the great circle of the head 22. The great circle refers to the circular intersection of the imaginary spherical surface B1 with a plane including the center of the sphere. The flat belt 25 has a substantially cylindrical shape with a central axis Q4 including the center of the imaginary spherical surface B1. In the illustrated example, the central axis Q4 intersects with the central axis Q3. More specifically, the flat belt 25 is inclined with respect to the central axis Q3, along which the screw body 21 extends. The flat belt 25 extends between the semispherical parts 23 and 24 and joins with them. The flat belt 25 has a smaller diameter than the imaginary spherical surface B1, to which the semispherical parts 23 and 24 conform. As described later, the flat belt 25 is used when the head 22 is inserted inside through the lower opening 5b of the outer member 5.

The interference part 26 has a shape deviating from the imaginary spherical surface B1, to which the semispherical parts 23 and 24 conform. In the illustrated example, the interference part 26 protrudes radially outward from the semispherical part 24. In the illustrated example, the interference part 26 protrudes radially outward from the imaginary spherical surface B1. In the illustrated example, the interference part 26 is located at the end of the head 22 opposite to the screw body 21, and protrudes along the central axis Q3 in a direction opposite to the direction in which the screw body 21 is located.

The top face of the interference part 26 has a substantially circular outer edge (also refer to FIG. 4). In a specific example, the interference part 26 has a substantially cylindrical shape with the central axis Q3. Inside the outer member 5, the interference part 26 is in contact with an inner peripheral surface 41a (more specifically, an interference surface 41c described later) of the inner member 4 to restrict the rotation range of the head 22 with respect to the connector 3. This will be described in detail later.

In the example of FIG. 4, the interference part 26 has a shape that can engage with a tool (not shown) for turning the screw 2 about the central axis Q3. In a more specific example, the interference part 26 has an engagement hole 27 on its head. The engagement hole 27 has a shape corresponding to the cross section of the tool as viewed along the central axis Q3. In the example of FIG. 4, the shape is a rounded star. Although the engagement hole 27 in FIG. 4 has six vertexes, the number of vertexes may be changed as appropriate. The engagement hole 27 receives a tool having substantially the same cross section. A medical worker may use the tool to turn the screw 2 about the central axis Q3 for embedding the screw 2 into the target bone. The engagement hole 27 may not be star-shaped, but may have another shape such as a slot, a cross, an H, a hexagon, or a square.

The outer member 5 has a substantially tubular shape with the central axis Q1. In a more specific example, the outer member 5 includes a tubular part 51 and a pair of side walls 52. The tubular part 51 is tubular. In the illustrated example, the tubular part 51 has a substantially cylindrical shape with the central axis Q1.

In the illustrated example, the tubular part 51 has an inner peripheral surface 51a including a cylindrical surface 51b, the spherical concave surface 51c, and a cylindrical surface 51d. The cylindrical surface 51b, the spherical concave surface 51c, and the cylindrical surface 51d are arranged in this order from top to bottom and continuous with one another. The lower edge of the cylindrical surface 51d defines the lower opening 5b of the outer member 5.

The cylindrical surface 51b has a substantially cylindrical shape with the central axis Q1. The cylindrical surface 51b has a smaller diameter than the imaginary spherical surface B1, to which the semispherical parts 23 and 24 of the head 22 conform.

The spherical concave surface 51c has the shape of concavity along the entire circumference of the inner peripheral surface 51a of the tubular part 51. The concavity of the spherical concave surface 51c conforms to the imaginary spherical surface B1 and has a diameter equal to or slightly greater than the diameter of the imaginary spherical surface B1. The central axis Q1 includes, for example, the center of the spherical concave surface 51c. The upper edge of the spherical concave surface 51c is continuous with the lower edge of the cylindrical surface 51b.

The cylindrical surface 51d has a substantially cylindrical shape with a central axis Q2 (refer to FIG. 3). In the illustrated example, the central axis Q2 intersects with the central axis Q1. The cylindrical surface 51d has a diameter smaller than the diameter of the imaginary spherical surface B1 and equal to or slightly greater than the diameter of the flat belt 25 of the head 22. The upper edge of the cylindrical surface 51d is continuous with the lower edge of the spherical concave surface 51c. The upper edge of the cylindrical surface 51d and the lower edge of the spherical concave surface 51c are inclined with respect to the central axis Q1. The lower edge of the cylindrical surface 51d defines the lower opening 5b of the outer member 5. In the illustrated example, the lower edge of the cylindrical surface 51d is located on a plane substantially orthogonal to the central axis Q1. More specifically, the upper edge and the lower edge of the cylindrical surface 51d are inclined with respect to each other, and the width (the length along the central axis Q2) differs at a different circumferential position. In FIG. 3, the width of the cylindrical surface 51d decreases toward the left and increases toward the right. The technical idea will be described later.

As described in detail later, the head 22 of the screw 2 is inserted into the outer member 5 through the lower opening 5b of the outer member 5 and rotatably fitted on the spherical concave surface 51c.

The pair of side walls 52 stand upright on the upper end of the tubular part 51. The pair of side walls 52 and the tubular part 51 may be formed from the same material and integrated together. The side walls 52 are opposite to each other with respect to the central axis Q1 and extend upward along the central axis Q1. The pair of side walls 52 have inner peripheral surfaces 52a facing each other and curved along an imaginary cylindrical surface with the central axis Q1. Each inner peripheral surface 52a has a thread groove (not shown). The side walls 52 face each other at a distance, and thus the space between the side walls 52 opens upward and extends through the outer member 5 in a direction intersecting with the central axis Q1.

The rod 130 is inserted between the pair of side walls 52 in a posture with its longitudinal direction aligned with the intersecting direction. In this state, the rod 130 is inserted with a portion in the longitudinal direction received between the side walls 52, and with the other portions extending from the opposite ends of the outer member 5.

The length of the pair of side walls 52 along the central axis Q1 is greater than the diameter of the rod 130. Thus, with the rod 130 inserted between the side walls 52, the pair of side walls 52 protrude upward from the rod 130.

The fastener 7 is, for example, a bolt and is screwed onto the inner peripheral surfaces 52a of the pair of side walls 52. The distal end of the fastener 7 is placed into contact with the rod 130 to press the rod 130 downward. The rod 130 is thus coupled to the connector 3.

The inner member 4 is located between the rod 130 and the head 22 of the screw 2 inside the outer member 5. The inner member 4 is movable along the central axis Q1 before the fastener 7 is screwed on. More specifically, the inner member 4 in this state is movable between a first position farther from the head 22 (hereafter, referred to as an upper position) and a second position nearer the lower opening 5b than the upper position (hereafter, referred to as a lower position). The inner member 4 may be in contact with the head 22 at the lower position. In this case, when the fastener 7 is screwed on, the inner member 4 is pressed downward with the rod 130. The press causes the inner member 4 to move to the lower position and be in contact with the head 22, pressing the head 22 downward. The head 22 is held by the inner member 4 and the lower part of the spherical concave surface 51c of the outer member 5.

In the illustrated example, the inner member 4 includes a lower part 41 and a pair of side walls 42. The lower part 41 has a shape that opens at least in its bottom. In the illustrated example, the inner member 4 has an internal space extending through the lower part 41 along the central axis Q1. The internal space opens in the top and the bottom of the lower part 41. This internal space is defined by the inner peripheral surface 41a of the lower part 41. In the illustrated example, the inner peripheral surface 41a includes a partial spherical surface 41b, the interference surface 41c, and a ceiling surface 41d.

Figure 5:
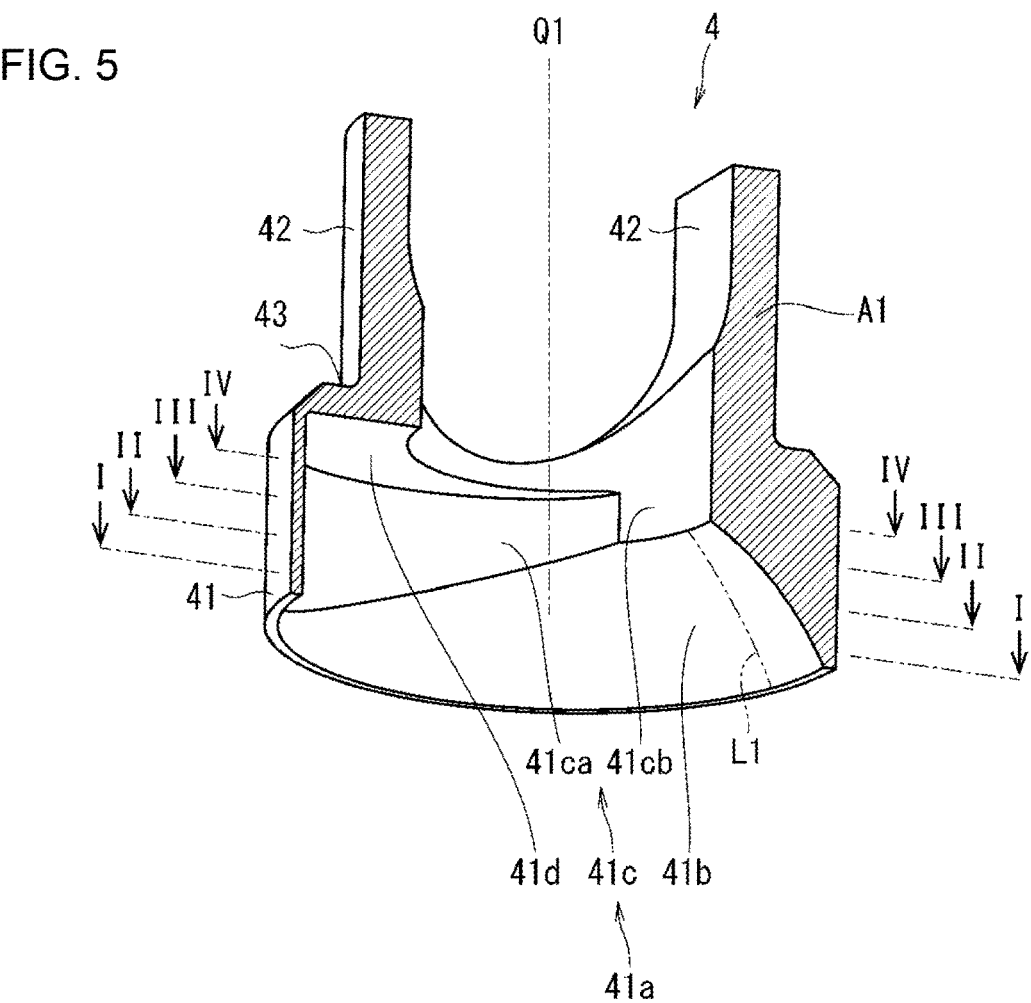
FIG. 5 illustrates a schematic perspective view of an example inner member.
Figure 6:
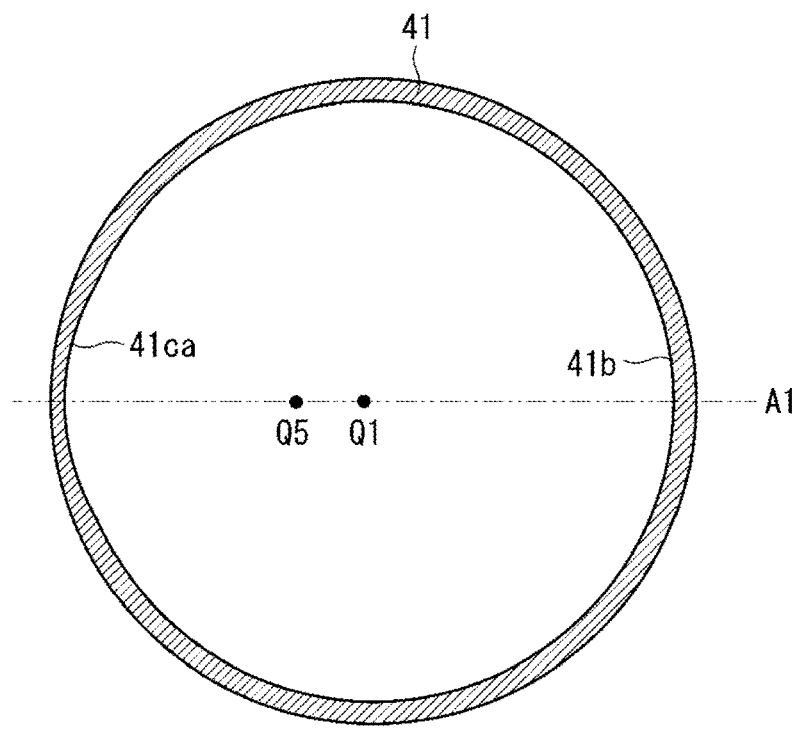
FIG. 6 illustrates a schematic imaginary cross-sectional view of the inner member taken along line I-I.
Figure 7:
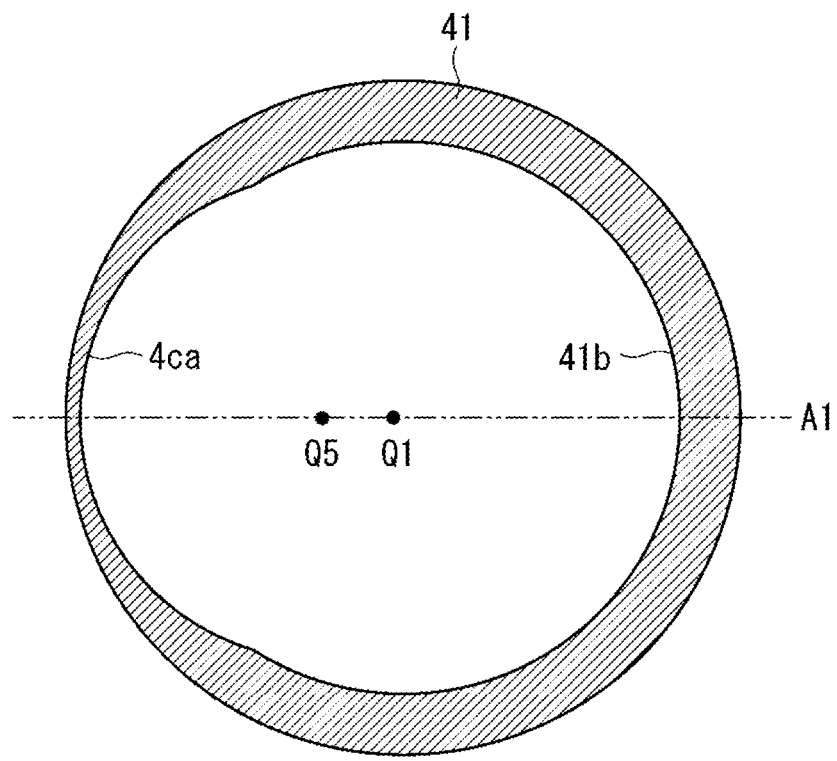
FIG. 7 illustrates a schematic imaginary cross-sectional view of the inner member taken along line II-II.
Figure 8:
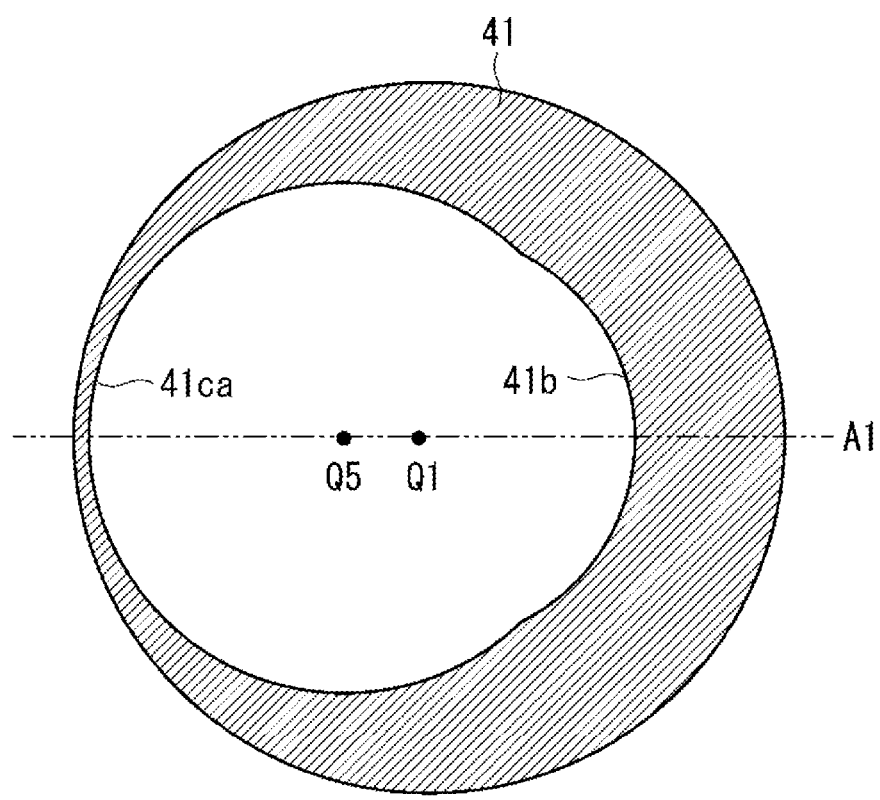
FIG. 8 illustrates a schematic imaginary cross-sectional view of the inner member taken along line III-III.
Figure 9:
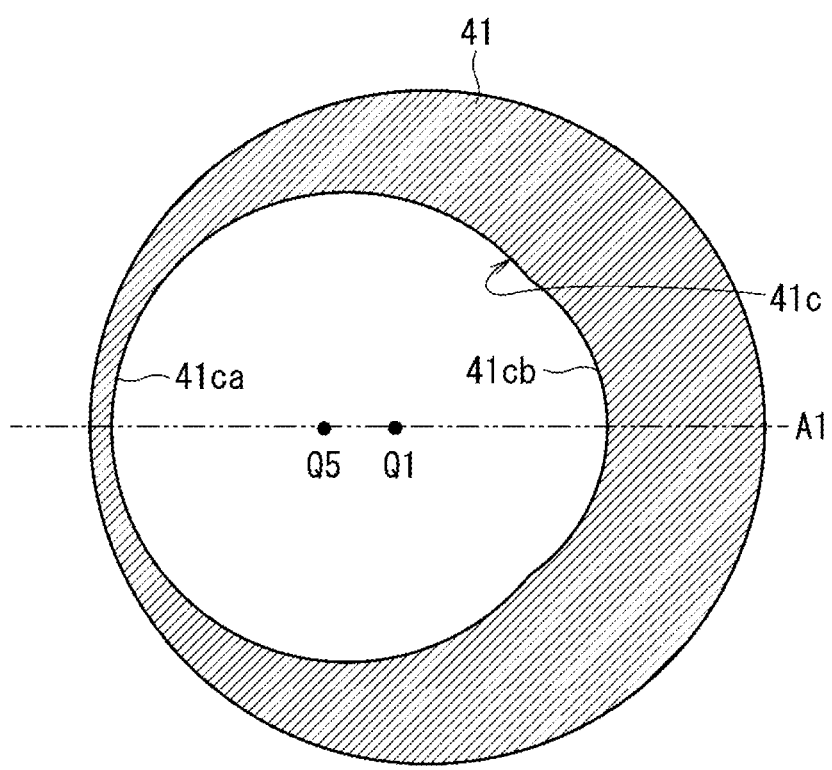
FIG. 9 illustrates a schematic imaginary cross-sectional view of the inner member taken along line IV-IV.

FIG. 5 is a perspective view of an example of the inner member 4. FIGS. 6 to 9 are schematic cross-sectional views of the lower part 41 of the inner member 4. FIG. 5 shows one of the two parts obtained by cutting the inner member 4 along an imaginary cross section A1. The imaginary cross section A1 is a plane including the central axis Q1. FIGS. 6 to 9 show cross sections orthogonal to the central axis Q1 from bottom to top. More specifically, FIGS. 6 to 9 are schematic imaginary cross-sectional views respectively taken along lines I-I, II-II, and IV-IV in FIG. 5. In other words, FIG. 6 shows the lowermost cross section of the lower part 41, whereas FIG. 9 shows the uppermost cross section of the lower part 41.

The partial spherical surface 41b is curved along the imaginary spherical surface B1 of the head 22 and to be in contact with the head 22. The partial spherical surface 41b, which is placed into contact with the head 22 from above, can also be the lower surface of the inner member 4. In the illustrated example, the partial spherical surface 41b is substantially symmetrical about the imaginary cross section A1. The imaginary cross section A1 is a plane including the central axis Q1 and indicated by a two-dot chain line in FIGS. 6 to 8. Referring to FIGS. 6 to 8, the partial spherical surface 41b is, in each cross section, in a portion of the inner member 4 in the circumferential direction, and the circumferential length of the partial spherical surface 41b shortens toward the top. The partial spherical surface 41b also approaches the central axis Q1 toward the top.

Referring to FIG. 5, the interference surface 41c extends upward from the upper edge of the partial spherical surface 41b. Referring also to FIGS. 2 and 3, the interference surface 41c defines a movement space H1 in which the interference part 26 of the head 22 moves. When the screw 2 is swung about the head 22 with respect to the connector 3, the interference part 26 moves within the movement space H1 about the center of the head 22. When the interference part 26 comes into contact with the interference surface 41c, the contact restricts the head 22 from rotating further. More specifically, the interference surface 41c restricts the rotation range of the head 22.

In the illustrated example, the interference surface 41c is also substantially symmetrical about the imaginary cross section A1 and includes an arc-shaped surface 41ca and an arc-shaped surface 41cb. The arc-shaped surface 41ca has a shape conforming to a cylindrical surface with a central axis Q5. However, the arc-shaped surface 41ca is in a portion of the inner member 4 in the circumferential direction. As illustrated in FIGS. 6 to 8, which are cross-sectional views taken through the partial spherical surface 41b, the arc-shaped surface 41ca has circumferential ends each continuous with the corresponding circumferential end of the partial spherical surface 41b. In these cross sections, the combination of the arc-shaped surface 41ca and the partial spherical surface 41b defines an annular shape. The central axis Q5 is an axis located on the imaginary cross section A1 and shifted from the central axis Q1, and is substantially parallel with the central axis Q1.

The arc-shaped surface 41cb is above the partial spherical surface 41b. The arc-shaped surface 41cb has a shape conforming to a cylindrical surface with the central axis Q1. However, the arc-shaped surface 41cb is in a portion of the inner member 4 in the circumferential direction. As illustrated in FIG. 9, which is a cross-sectional view taken above the partial spherical surface 41b, the arc-shaped surface 41cb has circumferential ends each continuous with the corresponding circumferential end of the arc-shaped surface 41ca. In the cross section, the combination of the arc-shaped surface 41ca and the arc-shaped surface 41cb defines an annular shape.

The upper edge of the arc-shaped surface 41ca joins with the outer edge of the ceiling surface 41d. The ceiling surface 41d is crescent as viewed along the central axis Q1 (also refer to FIG. 5). The ceiling surface 41d has an inner edge continuous with the lower edge of the inner peripheral surface of each side wall 42 described below, and the upper edge of the arc-shaped surface 41cb is also continuous with the lower edge of the inner peripheral surface of the side walls 42.

The pair of side walls 42 stand upright on the upper end of the lower part 41. The pair of side walls 42 and the lower part 41 may be formed from the same material and integrated together. The side walls 42 face each other in the direction in which the side walls 52 of the outer member 5 face each other. In the illustrated example, the direction in which the side walls 42 face each other is included in the imaginary cross section A1.

With the inner member 4 inside the outer member 5, the pair of side walls 42 are located between the side walls 52 of the outer member 5. The pair of side walls 42 receive the rod 130 between them. In this state, the rod 130 is inserted with a portion in the longitudinal direction received between the side walls 42, and with the other portions extending from the opposite ends of the inner member 4. With the rod 130 inserted, the upper ends of the pair of side walls 42 are located below the upper end of the rod 130.

In the illustrated example, the pair of side walls 42 stand upright inside the outer edge of the top surface of the lower part 41, and thus the outer peripheral surfaces of the pair of side walls 42 and the top surface of the lower part 41 define a step 43. For the outer member 5, the inner peripheral surfaces 52a of the pair of side walls 52 are located inside the inner peripheral surface 51a of the tubular part 51, and the inner peripheral surfaces 51a and 52a join with each other with a stopper surface 53a in between.

Thus, when the inner member 4 is moved upward inside the outer member 5, the outer edge of the top surface of the lower part 41 comes into contact with the stopper surface 53a of the outer member 5. The inner member 4 can thus avoid falling off the outer member 5 through the upper opening 5a.

In the illustrated example, the screw assembly 1 also includes a C-shaped member 6. The C-shaped member 6 has the shape of the letter C. More specifically, the C-shaped member 6 has a shape obtained by cutting a portion of a ring in the circumferential direction. The inner peripheral surface of the C-shaped member 6 has a flat cylindrical shape conforming to the flat belt 25 of the head 22, and the outer peripheral surface is curved along the imaginary spherical surface B1 of the head 22. The C-shaped member 6 has a width substantially equal to the width of the flat belt 25 of the head 22. The C-shaped member 6 has an inner diameter substantially equal to the diameter of the flat belt 25 or slightly smaller than the diameter of the flat belt 25.

The C-shaped member 6 is elastically deformable. The C-shaped member 6 is fitted to the flat belt 25 of the head 22 with its inner peripheral surface facing the flat belt 25 of the head 22. The structure including the head 22 and the C-shaped member 6 can have a shape closer to a sphere.

Figure 10:
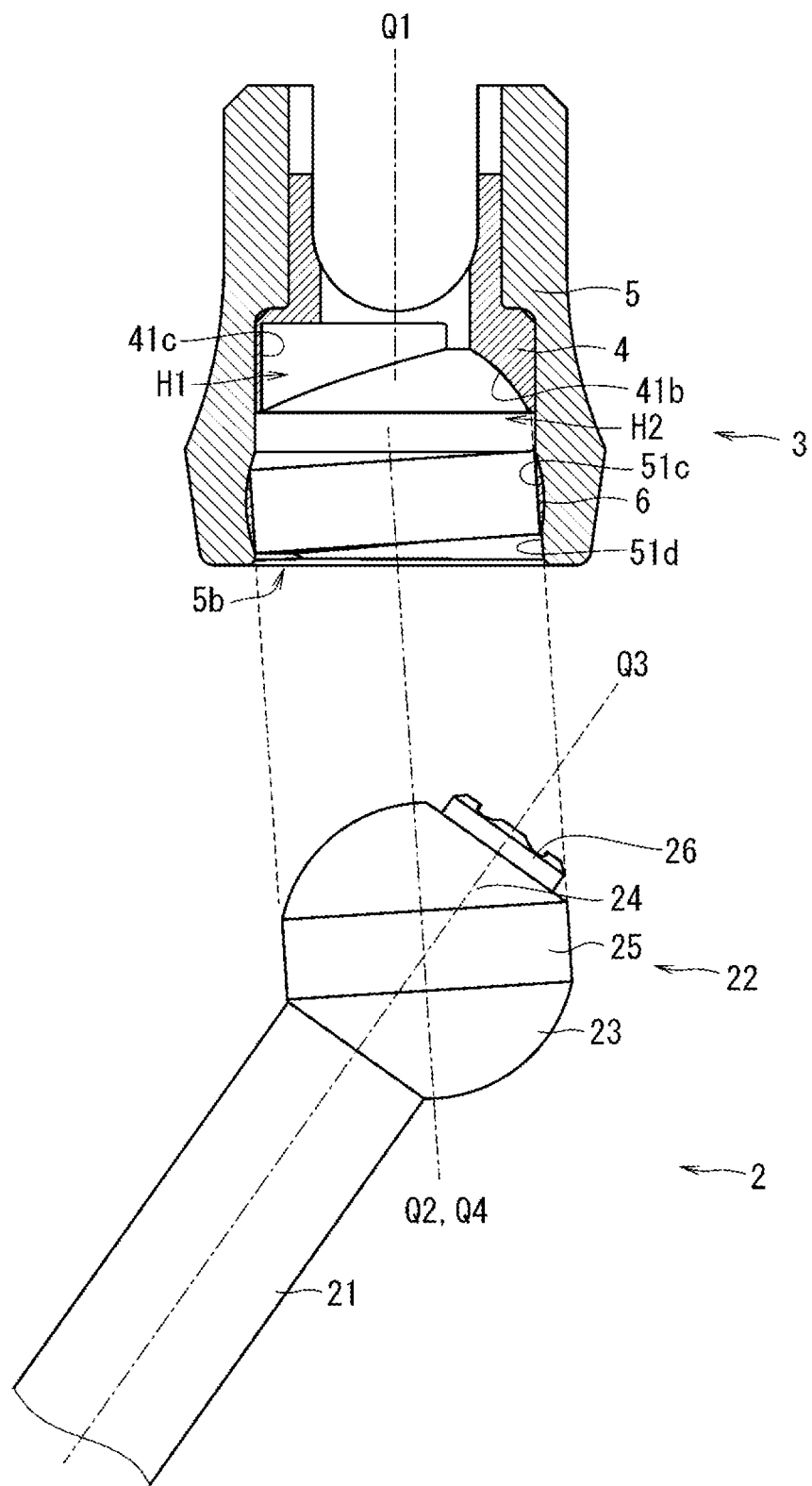
FIG. 10 illustrates a schematic cross-sectional view of the screw assembly showing an example assembling process.

A method for assembling the screw assembly 1 will now be described. FIG. 10 is a schematic diagram of the screw assembly 1 showing an example assembling process.

First, a medical worker inserts the inner member 4 into the outer member 5. More specifically, the inner member 4 is inserted through the lower opening 5b of the outer member 5. In this state, the inner member 4 is not fixed on the outer member 5 and can move along the central axis Q1. In the example of FIG. 10, the inner member 4 is at the upper position.

As illustrated in FIG. 10, the width of the cylindrical surface 51d (the width along the central axis Q2) differs at a different circumferential position. In FIG. 10, the width of the cylindrical surface 51d increases toward the right. Similarly, the partial spherical surface 41b of the inner member 4 has a length L1 that differs at a different circumferential position (the length in a cross section including the central axis Q1, also refer to FIG. 5). In FIG. 10, the length L1 of the partial spherical surface 41b increases toward the right. In other words, the medical worker inserts the inner member 4 into the outer member 5 in a posture in which a part of the partial spherical surface 41b with a greater length L1 is near a wider part of the cylindrical surface 51d.

The medical worker then inserts the C-shaped member 6 into the outer member 5. More specifically, the medical worker elastically deforms the C-shaped member 6 to place the ends of the C-shaped member 6 nearer each other. This allows the outer diameter of the C-shaped member 6 to be smaller than the diameter of the lower opening 5b of the outer member 5. The medical worker inserts the C-shaped member 6 with a smaller diameter inside through the lower opening 5b of the outer member 5 and fits it to the spherical concave surface 51c. In this state, the medical worker fits the C-shaped member 6 to the spherical concave surface 51c to place the inner peripheral surface of the C-shaped member 6 parallel to the cylindrical surface 51d of the outer member 5. Thus, the inner peripheral surface of the C-shaped member 6 and the cylindrical surface 51d define one continuous cylindrical surface.

The medical worker then inserts the head 22 of the screw 2 into the outer member 5. More specifically, the medical worker first inclines the screw 2 with respect to the outer member 5 to orient the flat belt 25 of the head 22 along the edge of the lower opening 5b of the outer member 5. In other words, the medical worker inclines the screw 2 to substantially align the central axis Q4 of the flat belt 25 with the central axis Q2 of the cylindrical surface 51d of the outer member 5. The medical worker adjusts the inclination of the screw 2 to allow the interference part 26 to face the partial spherical surface 41b of the inner member 4. In the example of FIG. 10, the interference part 26 faces the part of the partial spherical surface 41b that has a greater length L1. In FIG. 10, the screw 2 is inclined to place the interference part 26 to the right of the central axis Q1 and cause the screw body 21 to extend to the lower left.

The diameter of the flat belt 25 is equal to or smaller than the diameter of the cylindrical surface 51d. In the above state, the head 22 of the screw 2 can be inserted into or extracted from the outer member 5 through the lower opening 5b. The rotational position of the head 22 in this state with respect to the outer member 5 will be referred to as a reference rotational position.

The medical worker inserts the head 22 inside through the lower opening 5b of the outer member 5 while maintaining the reference rotational position. The insertion attaches the C-shaped member 6 to the flat belt 25 of the head 22, and then the C-shaped member 6 rotates together with the head 22.

Figure 11:
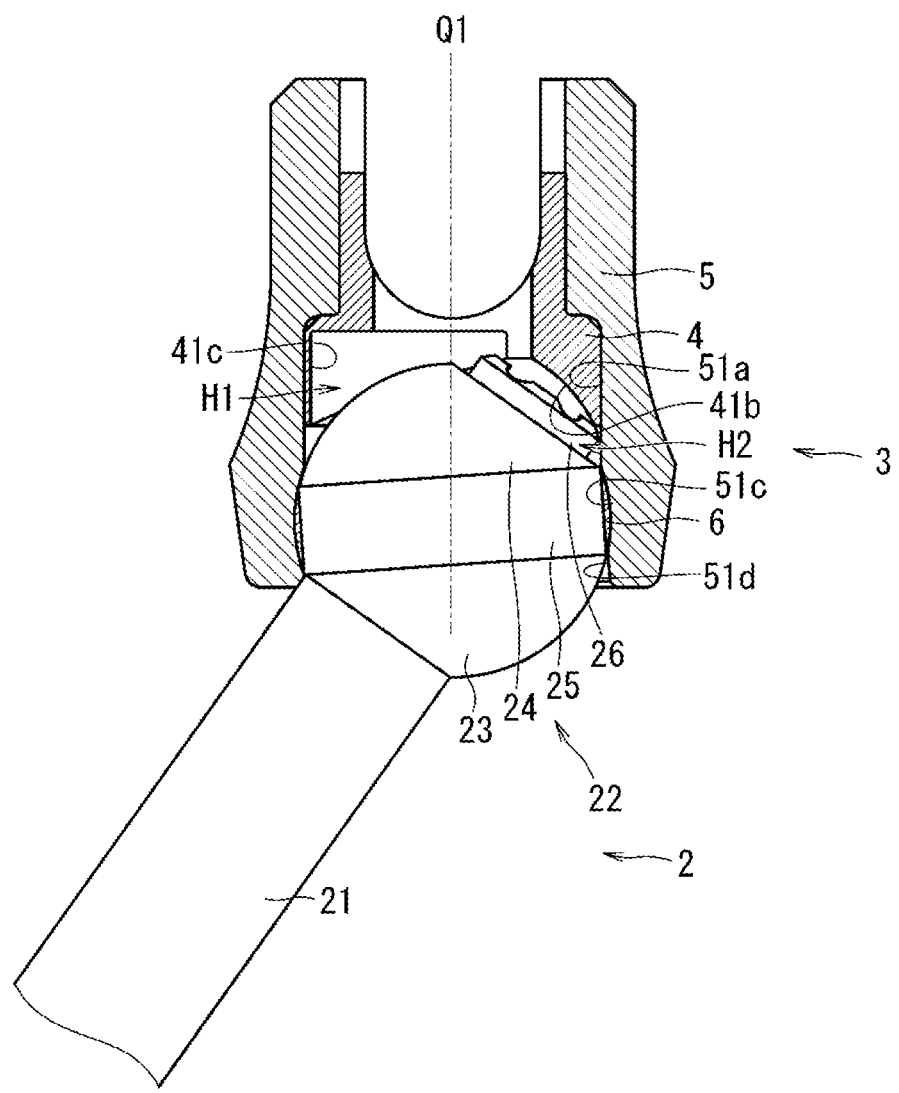
FIG. 11 illustrates a schematic cross-sectional view of the screw assembly showing an example assembling process.

FIG. 11 is a schematic cross-sectional view of the screw assembly 1 showing an example assembling process. In FIG. 11, the head 22 of the screw 2 is located inside the outer member 5, and the rotational position is the reference rotational position. In this state as well, the inner member 4 is at the upper position. The inner member 4 at the upper position does not restrict the rotation of the head 22.

The internal space of the outer member 5 occupied by the interference part 26 of the head 22 at the reference rotational position will be referred to as a predetermined space H2. When the inner member 4 is at the upper position, the inner member 4 is located above the predetermined space H2.

Figure 12:
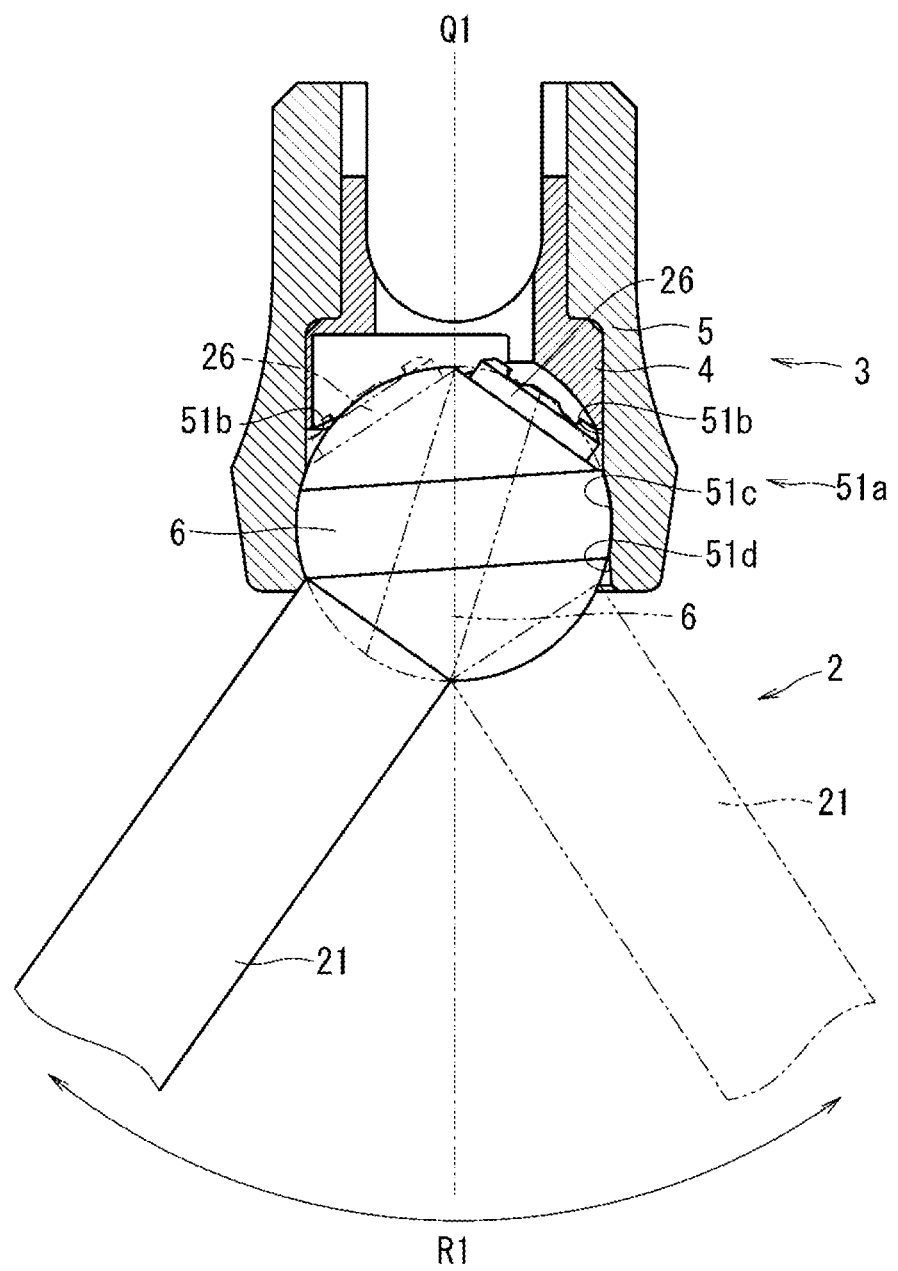
FIG. 12 illustrates a schematic diagram showing example rotation of the head of a screw with respect to a connector.

FIG. 12 is a schematic diagram showing example rotation of the head 22 with respect to the connector 3. In FIG. 12, the inner member 4 is at the upper position. In this state, the screw body 21 of the screw 2 is in contact with the lower end of the outer member 5, or the interference part 26 of the head 22 is in contact with the cylindrical surface 51b of the outer member 5, restricting the rotation range of the head 22 with respect to the connector 3. In FIG. 12, the rotation range of the head 22 is denoted by R1. The rotation range of the head 22 represents the range of the inclination angle of the screw body 21 with respect to the outer member 5.

The cylindrical surface 51b has a cylindrical shape with the central axis Q1, and also the lower end of the outer member 5 substantially has a circular shape about the central axis Q1, thus defining the rotation range R1 as being nearly isotropic about the central axis Q1.

Figure 13:
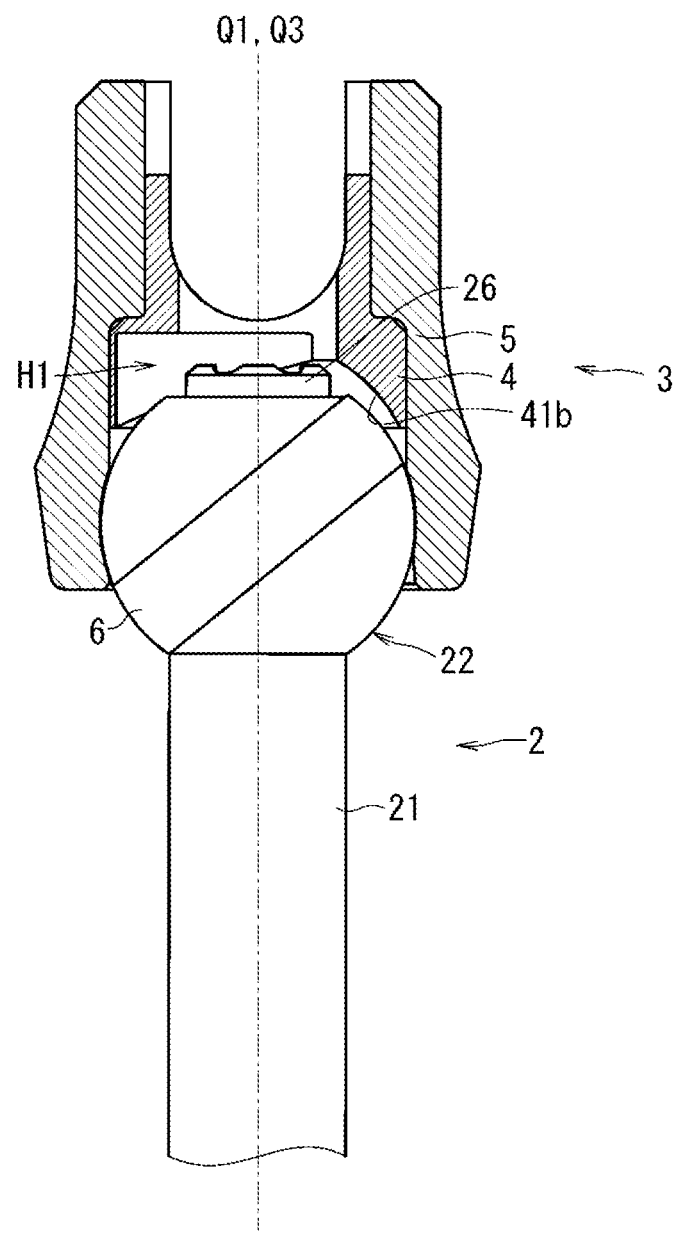
FIG. 13 illustrates a schematic cross-sectional view of the screw assembly showing an example assembling process.

The medical worker then displaces the screw 2 about the head 22 with respect to the outer member 5 to cause the interference part 26 of the head 22 to be retracted from the predetermined space H2. In other words, the medical worker displaces the screw 2 to move the interference part 26 in a direction parallel to the central axis Q1 to a rotational position not facing the partial spherical surface 41b of the inner member 4. FIG. 13 is a schematic cross-sectional view of the screw assembly 1 showing an example assembling process. In the example of FIG. 13, the interference part 26 of the head 22 does not face the partial spherical surface 41b of the inner member 4. In other words, the interference part 26 of the head 22 is located in the movement space H1. The central axes Q1 and Q3, which align with each other in the example of FIG. 13, may not align with each other. More specifically, the interference part 26 may be moved to a position at which the interference part 26 does not face the partial spherical surface 41b of the inner member 4.

Figure 14:
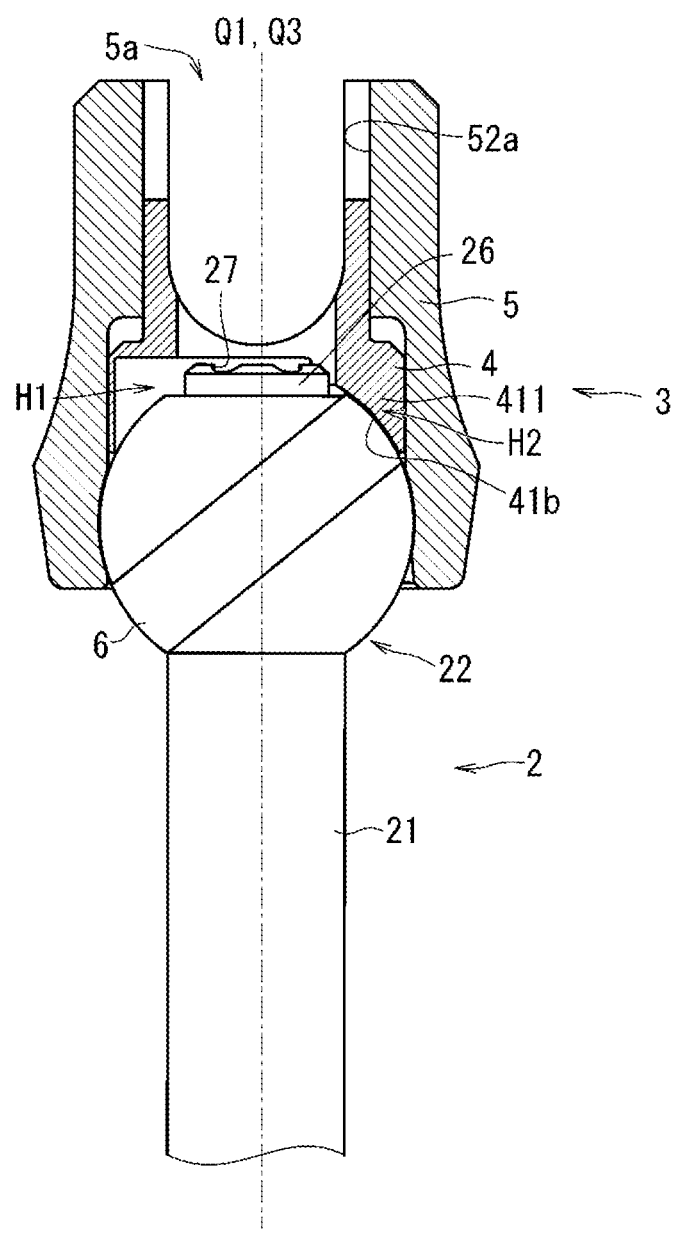
FIG. 14 illustrates a schematic cross-sectional view of the screw assembly showing an example assembling process.

The medical worker then moves the inner member 4 downward. FIG. 14 is a schematic cross-sectional view of the screw assembly 1 showing an example assembling process. In the example of FIG. 14, the inner member 4 is at the lower position. In this state, the partial spherical surface 41b of the inner member 4 is in contact with at least any one of the semispherical part 23, the semispherical part 24, and the C-shaped member 6 of the screw 2. A part of the inner member 4 (referred to as an interference part 411) is located in the predetermined space H2. The lower surface of the interference part 411 is the part of the partial spherical surface 41b that has a greater length L1. As described in detail later, the interference part 411 of the inner member 4 can interfere with the interference part 26 of the head 22.

Figure 15:
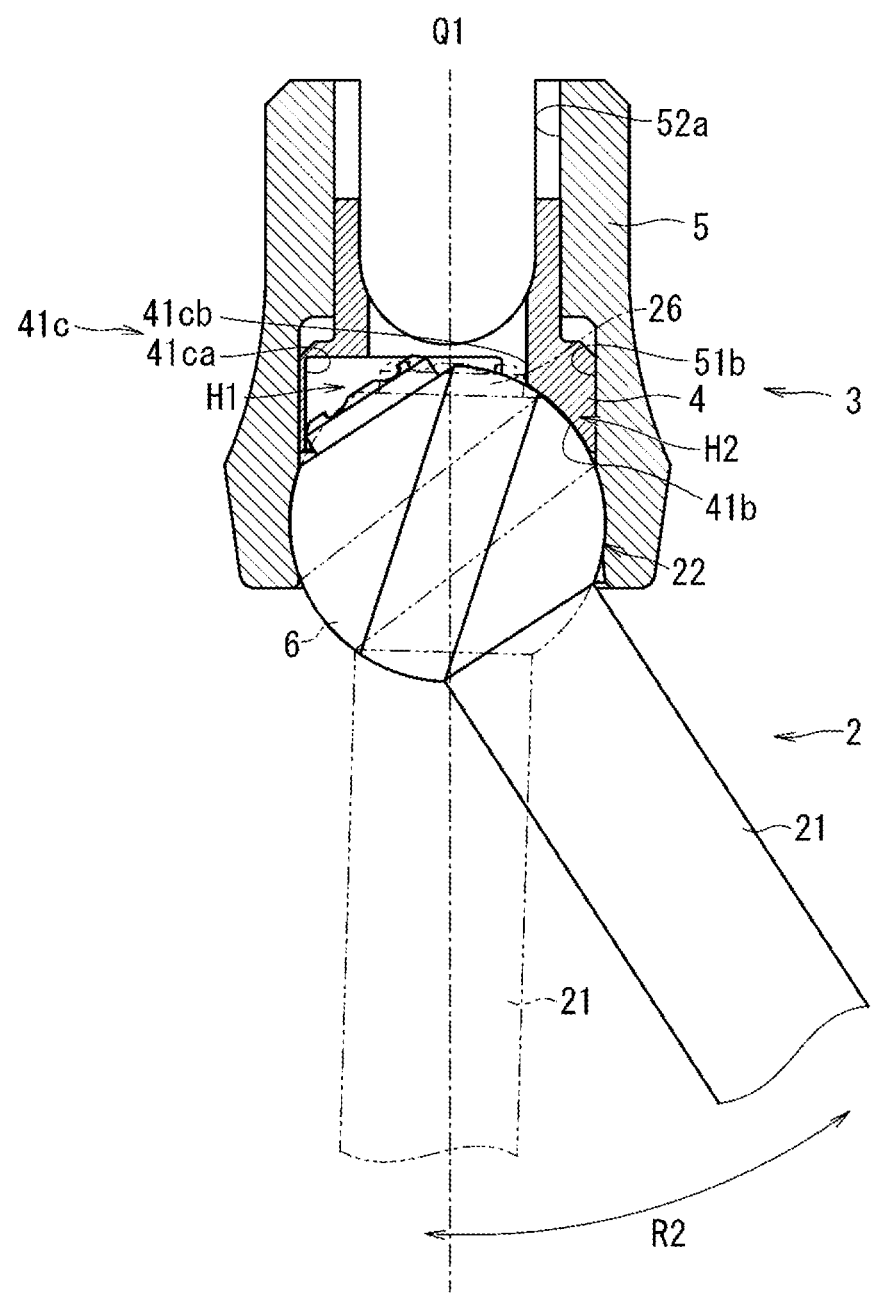
FIG. 15 illustrates a schematic diagram showing example rotation of the head of the screw with respect to the connector.

FIG. 15 is a schematic diagram showing example rotation of the head 22 with respect to the connector 3. In FIG. 15, the inner member 4 is at the lower position. In this state, the interference part 26 of the screw 2 is located in the movement space H1 surrounded by the interference surface 41c of the inner member 4. The inner member 4 can restrict the rotation range of the head 22. More specifically, the interference part 26 of the screw 2 comes into contact with the interference surface 41c of the inner member 4, restricting the rotation range of the head 22. In FIG. 15, the rotation range of the head 22 in this state is denoted by R2. The interference part 26 comes into contact with the interference surface 41c of the inner member 4, which is located inside the cylindrical surface 51b of the outer member 5. The rotation range R2 is thus smaller than the rotation range R1. Moreover, with the interference part 411 of the inner member 4 in the predetermined space H2, the interference part 26 cannot move to the predetermined space H2, and the head 22 cannot be at the reference rotational position. In other words, the rotation range R1 includes the reference rotational position, whereas the rotation range R2 does not include the reference rotational position.

Thus, with the inner member 4 at the lower position, the rotational position of the head 22 cannot be the reference rotational position, and the screw 2 cannot be extracted from the outer member 5.

As illustrated in FIG. 15, the rotation range R2 is defined off the central axis Q1 toward one side. In the example of FIG. 15, the screw body 21 can swing about the head 22 rightward from the central axis Q1 but cannot move greatly in the opposite direction. However, for the implant 100 illustrated in FIG. 1, the screw 2 of the right screw assembly 1 may extend rightward from the connector 3, and the screw 2 of the left screw assembly 1 may extend leftward from the connector 3. Thus, the rotation range R2 of the head 22 off the central axis Q1 toward one side does not affect the use of the screw assembly 1. In FIG. 15, the rotation range R2 allows rotation forward, or counterclockwise, up to about 35 degrees from the central axis Q1 at 0 degrees.

The screw assembly 1 is embedded into a bone in a human body in the manner described below. The medical worker first displaces the screw 2 about the head 22 with respect to the connector 3 to align the central axis Q3 with the central axis Q1 (refer to FIG. 14). In this state, the head face of the interference part 26 is visible through the upper opening 5a of the outer member 5. The medical worker then inserts a tool (not shown) into the upper opening 5a of the outer member 5 and engages it with the engagement hole 27 in the top face of the interference part 26. The medical worker turns the tool to turn the screw 2 about the central axis Q1, embedding the screw body 21 into the target bone.

The medical worker then adjusts the posture of the connector 3. More specifically, the medical worker rotates the connector 3 about the head 22 of the screw 2 to a rotational position appropriate to receive the rod 130. With the inner member 4 at the lower position, the connector 3 cannot be moved, and the head 22 cannot be placed at the reference rotational position. Thus, the connector 3 does not easily come off the head 22 during the operation. Under the gravity acting downward on the inner member 4, the inner member 4 can be maintained at the lower position by the gravity. In some cases, the inner member 4 may be maintained at the lower position under a frictional force between the inner member 4 and the outer member 5. In other cases, the inner member 4 and the outer member 5 may include a temporary engaging structure. The inner member 4 may be maintained at the lower position by the temporary engagement of the inner member 4 with the outer member 5.

The medical worker then inserts the rod 130 through the upper opening 5a of the outer member 5 and uses a predetermined tool to screw the fastener 7 to the inner peripheral surfaces 52a of the outer member 5. The fastener 7 thus presses the rod 130, the inner member 4, and the head 22 downward to fasten them together.

In this manner, the screw assembly 1 is implanted into the target bone, and the rod 130 is coupled to the screw assembly 1.

In the screw assembly 1, the inner member 4 can press the head 22 to retain the head 22 together with the outer member 5, and also can restrict the rotation range of the screw 2 with respect to the connector 3 to the rotation range R2, thus preventing the screw 2 from falling off easily. Thus, a simple operation allows the members of the screw assembly 1 to be less likely to separate from one another. This structure includes fewer members than when these functions are achieved by different members, and thus can be managed easily.

In the above example, the inner member 4 has a hollow extending along the central axis Q1 through the inner member 4. The hollow allows the medical worker to, with the inner member 4 and the head 22 of the screw 2 placed inside the outer member 5, turn the screw 2 using a predetermined tool (refer to FIG. 14). Thus, in this state, the screw 2 can be embedded into the target bone.

Additionally, the fastener 7 can be tightened to couple the rod 130 to the connector 3 and press the inner member 4 downward to the lower position. The tightening can thus fix the inner member 4 and the head 22 with the inner member 4 restricting the rotation range. The inner member 4 may be moved to the lower position with various methods other than by tightening the fastener 7.

In the above example, the partial spherical surface 41b of the inner member 4 is in contact with the head 22 and the C-shaped member 6. This achieves a larger contact area between the inner member 4 and the structure including the head 22 and the C-shaped member 6, allowing the structure to be fixed with a greater force.

In the above example, with the head 22 at the reference rotational position (refer to FIG. 11), the interference part 26 in the internal space of the outer member 5 is located in the predetermined space H2, which is nearer the inner peripheral surface 51a than the center of the internal space. More specifically, at the reference rotational position, the interference part 26 does not intersect with the central axis Q2. In other words, at the reference rotational position, the interference part 26 is located off the central axis. The movement space H1 is at least a part of the internal space of the outer member 5 that does not include the predetermined space H2. For a predetermined space H2 at the center of the internal space, or on the central axis Q1, the movement space H1 has a smaller volume, thus narrowing the rotation range R2. In the above example, the predetermined space H2 is located at the end of the internal space without intersecting with the central axis Q1, and thus the movement space H1 can be large, thus widening the rotation range R2.

In the above example, the flat belt 25 of the head 22 is inclined with respect to the central axis Q3, along which the screw body 21 extends (refer to FIG. 10). In other words, the central axis Q4 of the flat belt 25 intersects with the central axis Q3. Thus, at the reference rotational position, the screw body 21 extends in a direction inclined with respect to the central axis Q2 of the cylindrical surface 51d of the outer member 5. In the example of FIG. 12, the reference rotational position substantially corresponds to the left end of the rotation range R1.

As described above, the inner member 4 restricts the rotation range of the head 22 to the rotation range R2, which does not include the reference rotational position (refer to FIG. 15). As shown in FIGS. 12 and 15, the left end of the rotation range R2 is located to the right of the left end of the rotation range R1 (reference rotational position). The rotation range R2 is thus narrower than the rotation range R1.

Figure 16:
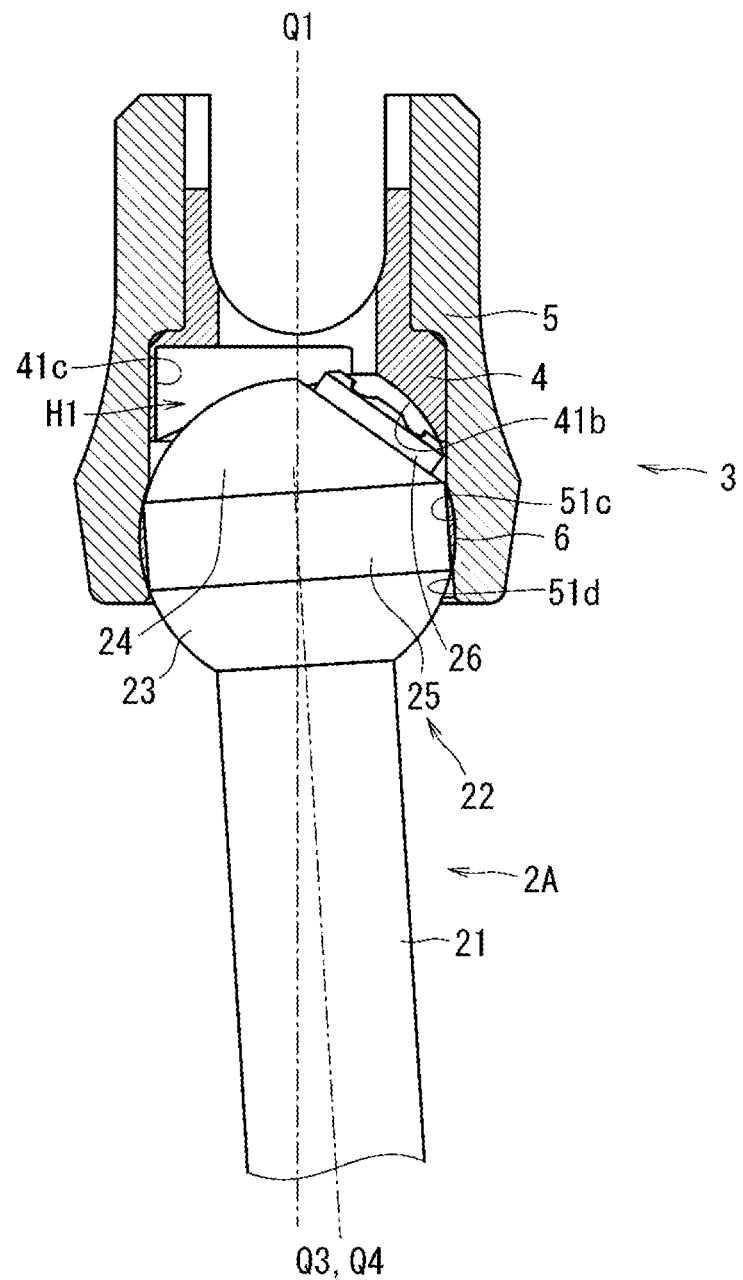
FIG. 16 illustrates a schematic diagram showing example insertion of the head of the screw into the connector.

The central axis Q4 of the flat belt 25 may align with the central axis Q3 of the screw body 21. FIG. 16 is a schematic diagram showing example insertion of a screw 2A as another example of the screw 2 into the connector 3. The screw 2A differs from the screw 2 in the direction in which the screw body 21 extends from the head 22. For the screw 2A, the central axis Q3, along which the screw body 21 extends, is substantially aligned with the central axis Q4 of the flat belt 25. In this case, at the reference rotational position, the screw body 21 extends in a direction nearer the central axis Q1.

Figure 17:
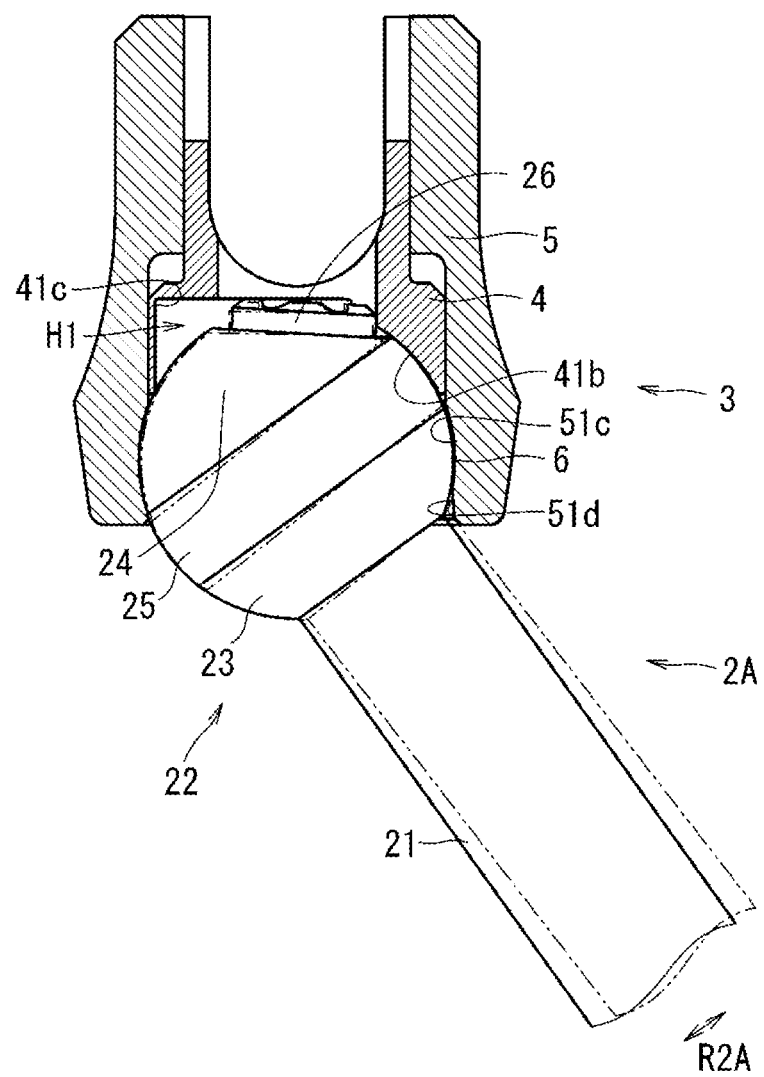
FIG. 17 illustrates a schematic diagram showing example rotation of the head of the screw with respect to the connector.

FIG. 17 is a schematic diagram showing example rotation of the head 22 of the screw 2A with respect to the connector 3. In the example of FIG. 17, the interference part 26 is retracted from the predetermined space H2 into the movement space H1, with the inner member 4 at the lower position. This restricts the rotation range of the head 22 to a rotation range R2A. As shown in FIGS. 15 and 17, the rotation range R2A is narrower than the rotation range R2. In other words, the inclination of the flat belt 25 of the head 22 with respect to the central axis Q3, along which the screw body 21 extends, allows the rotation range R2 to be wider.

In the above example, the interference surface 41c of the inner member 4 is curved along an imaginary cylindrical surface, and the interference part 26 of the head 22 has a top face with a circular outer edge. With these shapes, when the head 22 is rotated with the outer edge of the interference part 26 in contact with the interference surface 41c, the interference part 26 can slide smoothly along the interference surface 41c. The medical worker can thus displace the screw 2 smoothly about the head 22 with respect to the outer member 5.

In the above example, the central axis Q2 of the cylindrical surface 51d of the outer member 5 is inclined with respect to the central axis Q1 of the outer member 5. The effects produced by the inclination will now be described.

Figure 18:
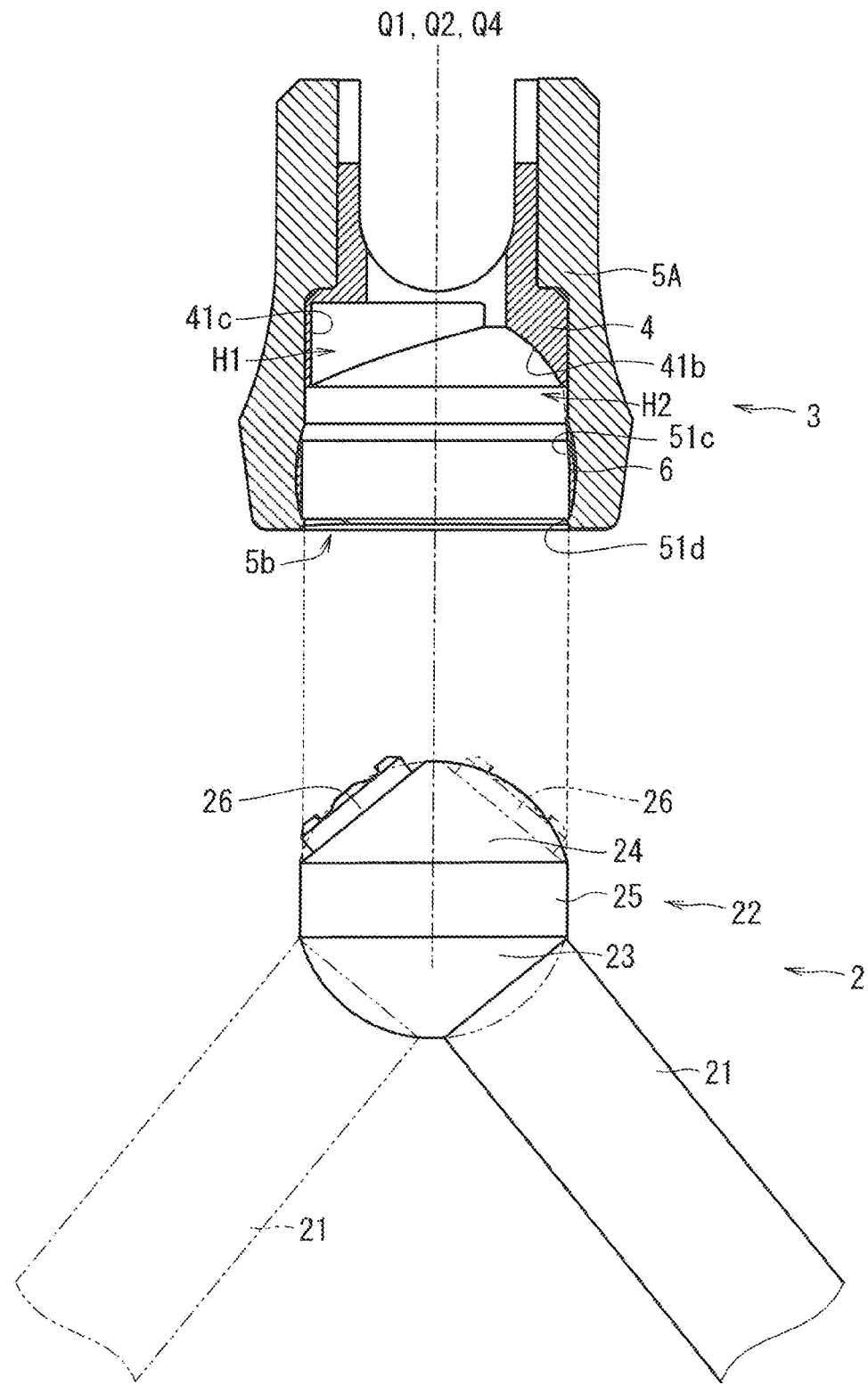
FIG. 18 illustrates a schematic diagram of another example outer member.

FIG. 18 is a schematic diagram of an outer member 5A as another example of the outer member 5. In the outer member 5A, the central axis Q2 of the cylindrical surface 51d aligns with the central axis Q1 of the outer member 5A.

In the example of FIG. 18, although the interference part 26 faces the movement space H1, the central axis Q4 of the flat belt 25 of the screw 2 aligns with the central axis Q2 of the cylindrical surface 51d. In this state, the head 22 of the screw 2 can be inserted through the lower opening 5b of the outer member 5A. Thus, the rotational position of the head 22 with respect to the outer member 5A indicated by solid lines in FIG. 18 is also a reference rotational position. However, in the example of FIG. 18, the interference part 26 faces the movement space H1. With the head 22 inserted in the outer member 5A in this state, the rotational position of the head 22 can be the reference rotational position in FIG. 18 after the inner member 4 is moved to the lower position. More specifically, the inner member 4 cannot appropriately restrict the rotation range of the screw 2.

For the outer member 5A, the head 22 of the screw 2 may be inserted into the outer member 5A in the posture indicated by two-dot chain lines (imaginary lines). More specifically, with the interference part 26 in the posture in which the interference part 26 faces the predetermined space H2, the head 22 may be inserted into the outer member 5A. As illustrated in FIG. 14, the screw 2 may then be displaced about the head 22 to place the interference part 26 in the movement space H1. As illustrated in FIG. 15, the inner member 4 may be moved to the lower position. In this manner, the rotation range of the screw 2 can be restricted to the rotation range R2, which does not include the reference rotational position.

However, for the outer member 5A, the head 22 of the screw 2 can be inserted into the outer member 5A in a posture in FIG. 16 in which the inner member 4 cannot restrict the rotation range, and thus the medical worker may fail in the assembling process. More specifically, the outer member 5A may not improve workability greatly.

Figure 19:
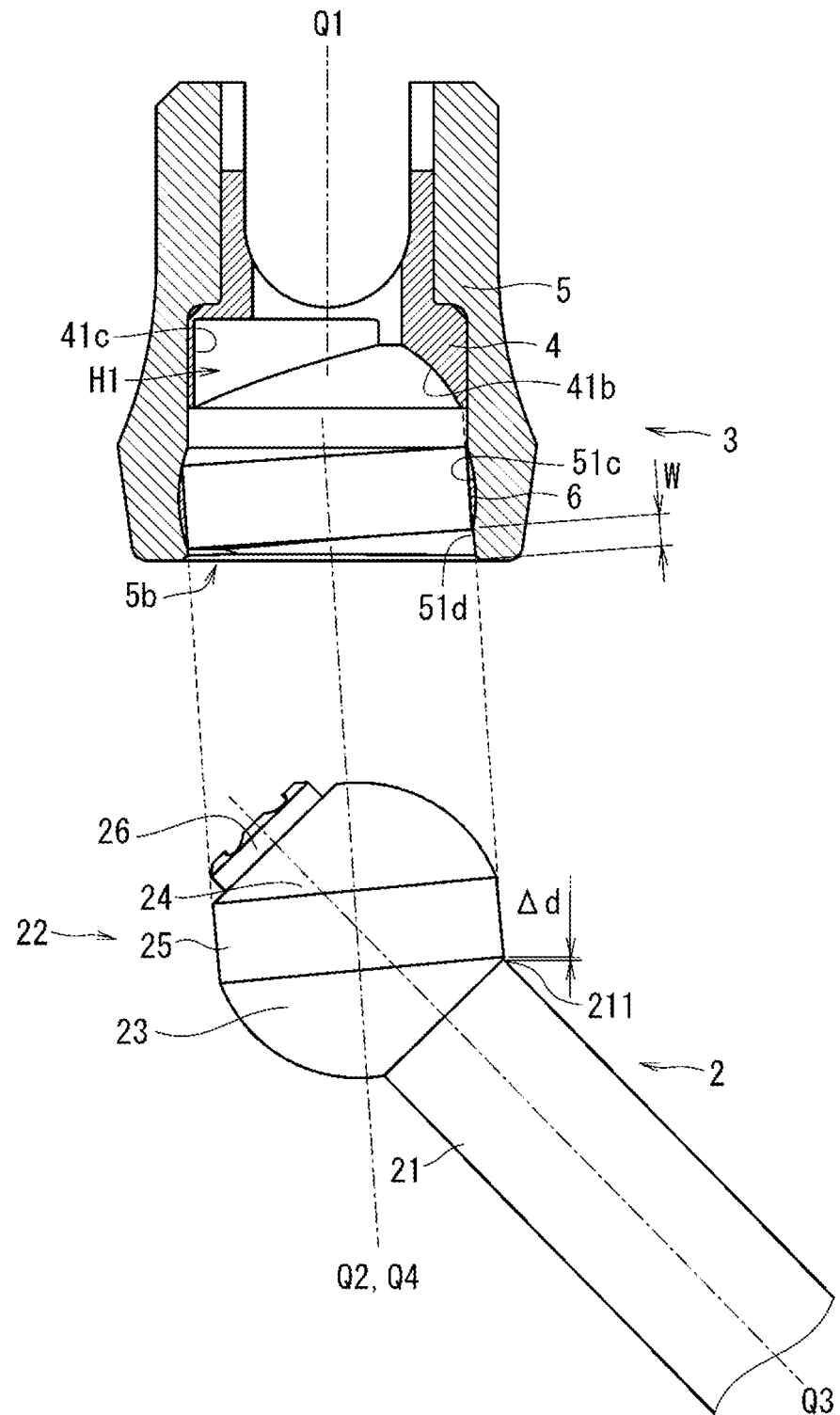
FIG. 19 illustrates a schematic diagram showing example insertion of the head of the screw into the connector.

In contrast, with the central axis Q2 of the cylindrical surface 51d of the outer member 5 inclined with respect to the central axis Q1 of the outer member 5, the head 22 cannot be inserted into the outer member 5 in a posture in which the interference part 26 faces the movement space H1. FIG. 19 is a schematic diagram showing example insertion of the head 22 of the screw 2 into the outer member 5. In the example of FIG. 19, the interference part 26 of the screw 2 faces the movement space H1. The central axis Q4 of the flat belt 25 of the screw 2 aligns with the central axis Q2 of the cylindrical surface 51d of the outer member 5.

In this posture, the screw body 21 extends with respect to the central axis Q1 in a direction of increasing width of the cylindrical surface 51d of the outer member 5 (width along the central axis Q2). In FIG. 19, the screw body 21 extends to the lower right. Thus, a part 211 of the screw body 21 nearest the flat belt 25 is located in a wider part of the cylindrical surface 51d (the right side of FIG. 19). Moreover, the screw body 21 and the flat belt 25 have a minimum distance Δd (minimum value of distance along the central axis Q2) smaller than the maximum width W of the cylindrical surface 51d.

Figure 20:
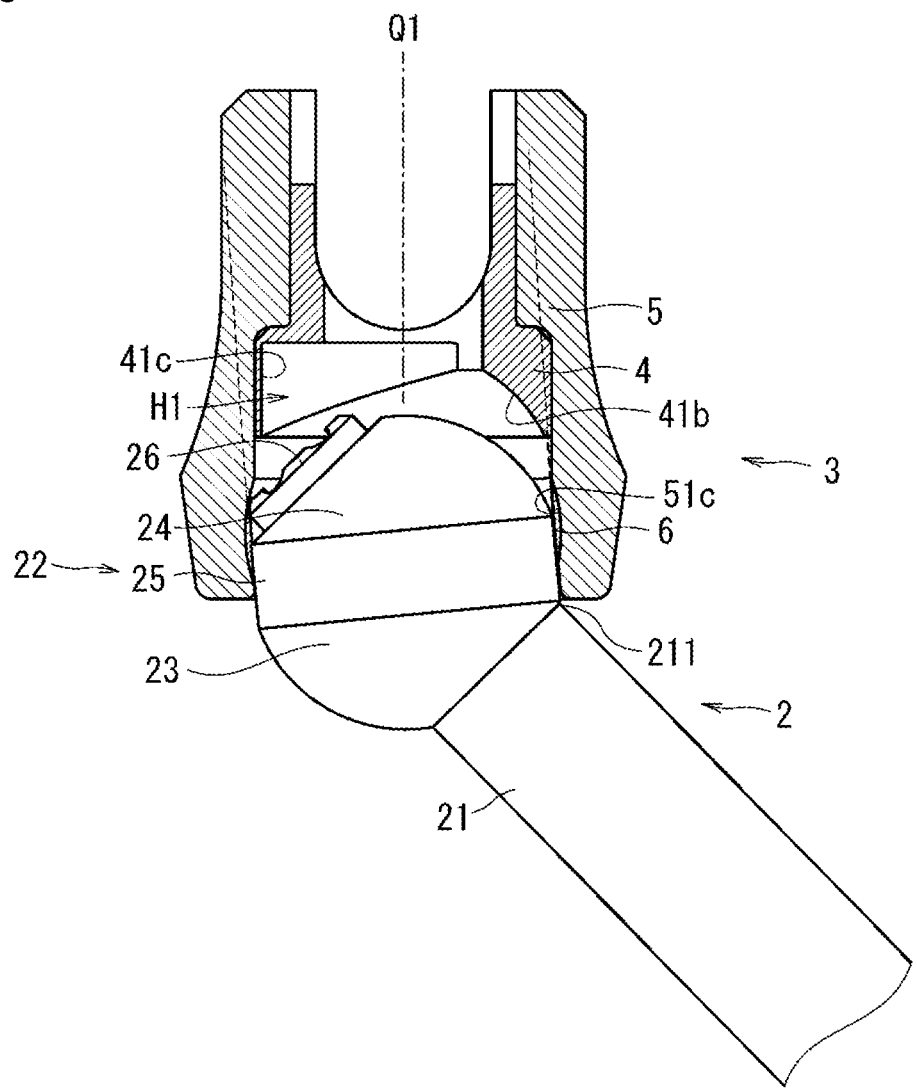
FIG. 20 illustrates a schematic diagram showing example insertion of the head of the screw into the connector.

FIG. 20 is a schematic diagram showing example insertion of the screw 2 into the outer member 5. When the head 22 is inserted through the lower opening 5b of the outer member 5, as illustrated in FIG. 20, the part 211 of the screw body 21 comes into contact with the lower end of the outer member 5 before reaching an appropriate position. More specifically, in this posture, the head 22 cannot be inserted into the outer member 5.

The medical worker turns the head 22 about the central axis Q2 to insert the head 22 into the outer member 5. The head 22 is then inserted into the outer member 5 in the posture in FIG. 10. After the head 22 is inserted, as described above, the screw 2 is displaced about the head 22 to place the interference part 26 in the movement space H1, and the inner member 4 is moved downward. In this manner, the rotation range of the head 22 is restricted to the rotation range R2, which does not include the reference rotational position. In other words, the head 22 of the screw 2 is prevented from easily falling off through the lower opening 5b of the outer member 5.

As described above, in a posture in which the inner member 4 cannot function, the outer member 5 prevents the head 22 from being inserted into the outer member 5, thus allowing the medical worker to assemble the screw assembly 1 easily with improved workability.

In the above example, the screw assembly 1 includes the C-shaped member 6. The structure including the head 22 and the C-shaped member 6 can have a shape closer to a sphere. This can increase the contact area between the structure and the partial spherical surface 41b of the inner member 4, allowing the head 22 to be retained with a greater force.

The screw assembly 1 have been described in detail as above, but the foregoing structures are illustrative in all respects, and the disclosure is not limited to the above structures. All the features of the embodiments and the modifications described above may be combined in use unless any contradiction arises. Many modifications not specifically described above may be implemented without departing from the scope of the disclosure.

For example, the outer edge of the interference part 26 may not be circular but may be elliptical. In some cases, the outer edge of the interference part 26 may have the shape of a rounded star. The star may have vertexes on a predetermined imaginary circle. This shape also allows the head 22 to be turned smoothly with the outer edge of the interference part 26 in contact with the interference surface 41c of the inner member 4. In this case, the screw 2 can be turned about the central axis Q3 with a nut driver having substantially the same shape as the outer edge of the interference part 26.

Unlike in the above examples, the interference part 26 may not protrude radially outward from the head 22. More specifically, the interference part 26 of the head 22 may have any form in contact with the inner member 4 at the lower position to restrict the rotation range of the head 22 to the rotation range R2, which does not include the reference rotational position. For example, the interference part 26 may be a radially inward recess in the head 22. In this case, the inner member 4 may also include an interference part loosely inserted in the recess at the lower position. When the inner member 4 is at the upper position, the interference part is located outside the recess and not in contact with the head 22. The interference part is, for example, a rod-shaped protrusion. When the interference part is loosely inserted in the recess, the head 22 is rotatable within a rotation range defined by the gap between the interference part and the recess. More specifically, the contact of the interference part with the edge of the recess restricts the rotation range of the head 22 to the rotation range R2.

Figure 23:
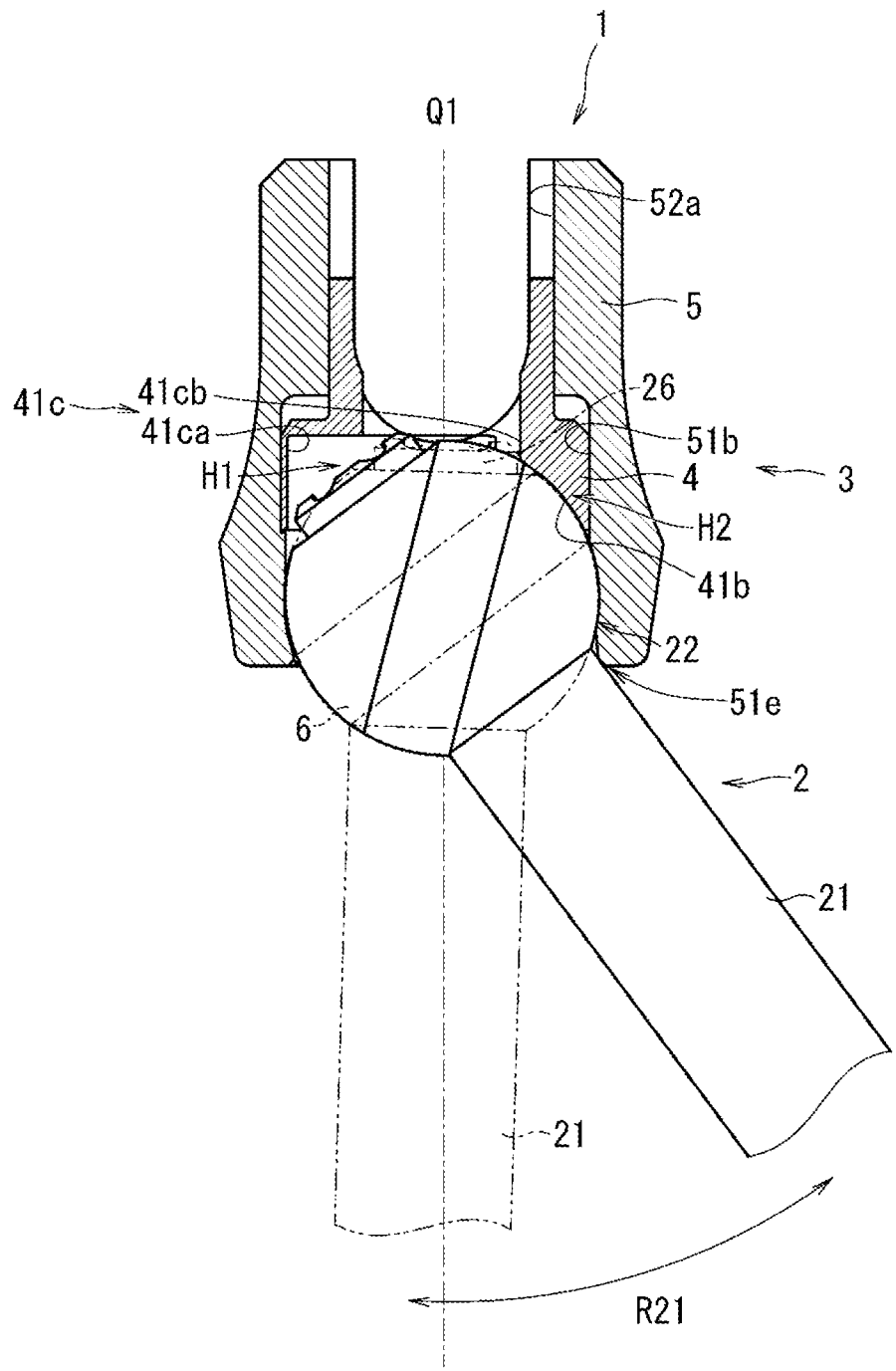
FIG. 23 illustrates a schematic diagram of an example screw assembly.

FIG. 23 is a schematic cross-sectional view of an example screw assembly 1 according to another embodiment. In the example of FIG. 23, the inner member 4 is at the lower position, and the rotation of the head 22 toward the reference rotational position is restricted by the contact between the inner member 4 and the interference part 26. In the example of FIG. 23, the leftmost position of a rotation range R21 is defined by the contact between the inner member 4 and the interference part 26.

In the example of FIG. 23, the screw body 21 can rotate about the head 22 to be in contact with a part of the lower end of the outer member 5. More specifically, in the example of FIG. 23, the arc-shaped surface 41ca of the inner member 4 has a larger diameter. Thus, the head 22 rotated from left to right in FIG. 23 places the screw body 21 into contact with the lower end of the outer member 5 before the interference part 26 comes into contact with the arc-shaped surface 41ca of the inner member 4. In other words, in the present embodiment, the rotation range R21 of the head 22 is also defined by the contact between the screw body 21 and the lower end of the outer member 5. In the example of FIG. 23, although the rightmost position of the rotation range R21 is defined by the contact between the screw body 21 and the lower end of the outer member 5, the inner member 4 is not in contact with the interference part 26 at this position.

Figure 24:
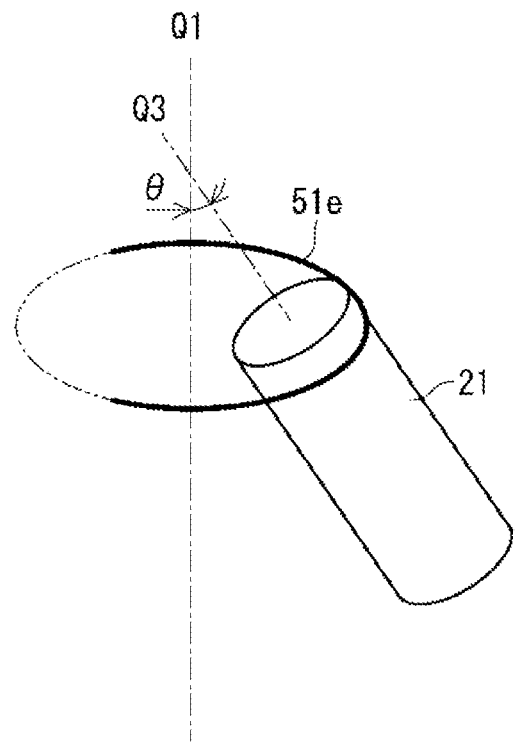
FIG. 24 illustrates a schematic diagram of the lower end of an outer member, showing the part to be in contact with the screw body.

FIG. 24 is a schematic diagram of the lower end of the outer member 5, showing a part 51e to be in contact with the screw body 21. In the example of FIG. 24, the part 51e is arc-shaped, and the plane along the part 51e is substantially orthogonal to the central axis Q1. The screw body 21 is rotatable about the head 22 within the range along the arc of the part 51e. Unlike the example of FIG. 24, the part 51e of the outer member 5 may not be substantially orthogonal to the central axis Q1.

Figure 25:
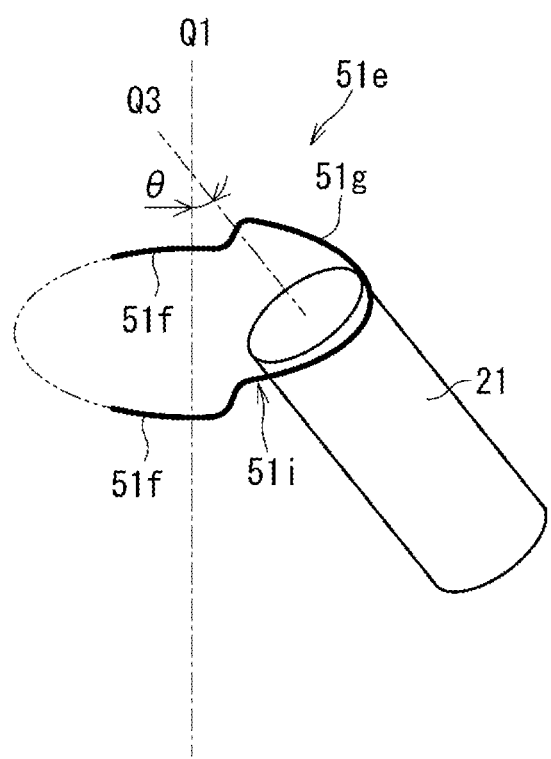
FIG. 25 illustrates a schematic diagram of the lower end of an outer member, showing the part to be in contact with the screw body.

FIG. 25 is a schematic diagram of another example of a part 51e of an outer member 5 according to a modification. In the example of FIG. 25, the part 51e includes a first area 51f and a second area 51g. The second area 51g is nearer the first opening 5a of the outer member 5 than the first area 51f. In FIG. 25, the second area 51g is located above the first area 51f. In a specific example, the part 51e has a recess 51i toward the first opening 5a, and the recess 51i corresponds to the second area 51g, and the portion of the part 51e extending from both ends of the recess 51i corresponds to the first area 51f.

This structure can partially enlarge the rotation range of the screw body 21 defined by the part 51e of the outer member 5. In the example of FIG. 25, the rotation range of the screw body 21 can be widened in the second area 51g. In other words, when the screw body 21 is in contact with the second area 51g, the angle θ formed by the central axis Q1 and the central axis Q3 of the screw body 21 may be greater than the angle θ formed when the screw body 21 is in contact with the first area 51f.

Figure 26:
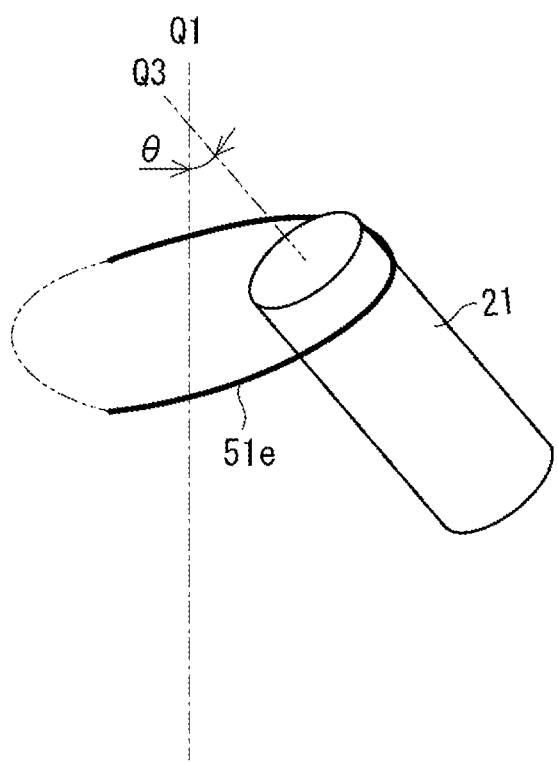
FIG. 26 illustrates a schematic diagram of the lower end of an outer member, showing the part to be in contact with the screw body.

FIG. 26 is a schematic diagram of an example outer member 5 according to a modification. As illustrated in FIG. 26, a part 51e may be inclined with respect to a plane orthogonal to the central axis Q1 of the outer member 5. More specifically, the part 51e is on a predetermined imaginary plane, and the imaginary plane may be inclined with respect to a plane orthogonal to the central axis Q1. In the example of FIG. 26, the part 51e has the shape of a partial ellipse and is inclined from both ends toward the first opening 5a (in FIG. 26, upward along the central axis Q1). In this structure, the upper limit of the rotation range of the screw body 21 defined by the lower end of the outer member 5 can be raised in one side. In FIG. 26, the upper limit of the rotation range of the screw body 21 can be increased in the right side. The imaginary plane has an inclination angle of, for example, 1 to 20 degrees with respect to the plane orthogonal to the central axis Q1.

For the part 51e inclined with respect to the plane orthogonal to the central axis Q1 (FIG. 26), the part 51e includes the first area 51f and the second area 51g. For example, when the first area 51f is used as both ends of the part 51e, the part between the ends can be the second area 51g.

Although the outer member 5 is outside the inner member 4 and is thus named as being outer, another member may be placed outside the outer member 5.

Figure 21:
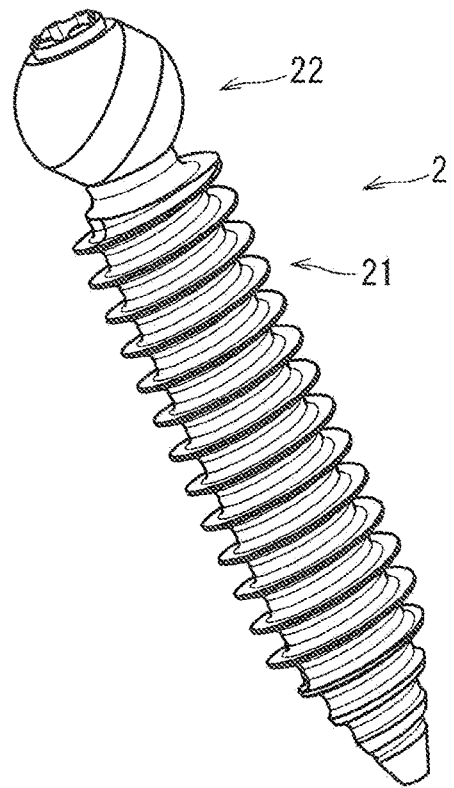
FIG. 21 illustrates a schematic diagram of an example internal fixation member body being a screw.
Figure 22:
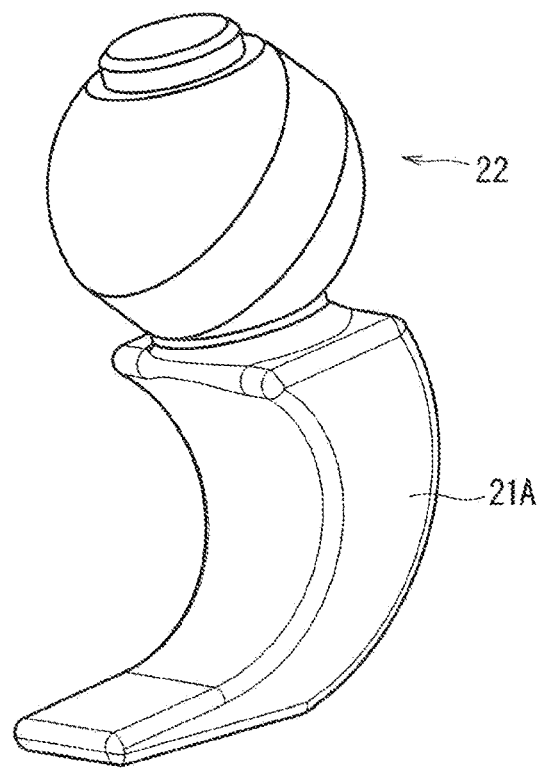
FIG. 22 illustrates a schematic diagram of an example internal fixation member body being a hook.

Unlike in the above example, the internal fixation member body may not be the screw body 21 shown in FIG. 21. The internal fixation member body may have any shape fixable to a bone in a living body. The shape of the internal fixation member body may be changed as appropriate. For example, the internal fixation member body may be a hook 21A to be engaged in a bone in a living body, as shown in FIG. 22. The hook 21A has the shape of a curved nail. The hook 21A engages with the outer surface of the bone. The internal fixation member body may also be a pin to be pressed or driven into a bone in a living body. The pin has the shape of, for example, a pointed rod. The pin is pressed or driven from its tip into the bone. In FIG. 2, the thread of the screw body 21 is not shown, and thus an internal fixation member in which the internal fixation member body is a pin is similar in shape to the screw 2 shown in FIG. 2. However, the head 22 of this internal fixation member may not have the engagement hole 27.

The internal fixation member body in the above example, which is implanted in the human body, may also be implanted in a nonhuman animal.

The invention claimed is:

1. An internal fixation member set for a bone, the internal fixation member set comprising:
   an internal fixation member including an internal fixation member body and a head located on an end of the internal fixation member body;
   an outer member having a first opening and a second opening, and rotatably retaining the head; and
   an inner member being inside the outer member and nearer the first opening than the head, the inner member being movable between a first position farther from the head and a second position nearer the second opening than the first position,
   wherein the inner member includes a first interference part configured to interfere with the head,
   the head includes a second interference part configured to interfere with the first interference part of the inner member,
   the head has a first rotation range with the inner member at the first position and a second rotation range with the inner member at the second position, and the second rotation range is smaller than the first rotation range with an interference between the first interference part and the second interference part,
   the head has a reference rotational position at which the head is insertable into or extractable from the outer member, and the reference rotational position is included in the first rotation range and is not included in the second rotation range,
   the internal fixation member body includes a screw shaft, and
   the second interference part has an engagement hole engageable with a tool for turning the screw shaft.

2. The internal fixation member set according to claim 1, wherein
   the second interference part protrudes in a direction opposite to a direction in which the internal fixation member body is located,
   with the head at the reference rotational position, the second interference part is in a predetermined space inside the outer member,
   the inner member is movable to the second position with the second interference part retracted from the predetermined space in response to the head being rotated with respect to the outer member, and
   with the inner member at the second position, the first interference part of the inner member is in the predetermined space.

3. The internal fixation member set according to claim 2, wherein
   the second interference part has a top face with a circular outer edge, and the first interference part has an interference surface to be in contact with the outer edge of the top face of the second interference part, and the interference surface is curved along an imaginary cylindrical surface.

4. The internal fixation member set according to claim 2, wherein with the head at the reference rotational position, the second interference part does not intersect with a central axis of the outer member.

5. The internal fixation member set according to claim 1, wherein the internal fixation member body includes a screw shaft, a hook, or a pin.

6. The internal fixation member set according to claim 1, wherein
the internal fixation member set includes a fastener insertable into the first opening of the outer member, and
the fastener is tightened to press the inner member against the head.

7. The internal fixation member set according to claim 6, wherein the inner member has an inner peripheral surface being a partial spherical surface conforming to an imaginary spherical surface of the head, and the partial spherical surface is to be in contact with a spherical part of the head.

8. The internal fixation member set according to claim 1, wherein the outer member has an end having the second opening, the end includes a portion to be in contact with the internal fixation member body with the inner member at the second position, and the portion includes a first area and a second area nearer the first opening than the first area.

9. The internal fixation member set according to claim 8, wherein the portion of the end of the outer member is inclined at an angle of 1 to 20 degrees with respect to a plane orthogonal to a movement direction of the inner member.

10. An internal fixation member set for a bone, the internal fixation member set comprising:
an internal fixation member including an internal fixation member body and a head located on an end of the internal fixation member body;
an outer member having a first opening and a second opening, and rotatably retaining the head; and
an inner member being inside the outer member and nearer the first opening than the head, the inner member being movable between a first position farther from the head and a second position nearer the second opening than the first position,
wherein the inner member includes a first interference part configured to interfere with the head,
the head includes a second interference part configured to interfere with the first interference part of the inner member,
the head has a first rotation range with the inner member at the first position and a second rotation range with the inner member at the second position, and the second rotation range is smaller than the first rotation range with an interference between the first interference part and the second interference part, and
the head has a reference rotational position at which the head is insertable into or extractable from the outer member, and the reference rotational position is included in the first rotation range and is not included in the second rotation range, wherein
the outer member has an inner peripheral surface including
a spherical concave surface on which the head fits, and
a cylindrical surface nearer the second opening than the spherical concave surface,
the cylindrical surface has an edge nearer the second opening, the edge defines the second opening of the outer member, and
the cylindrical surface has a central axis inclined with respect to a central axis of the outer member.

11. An internal fixation member set for a bone, the internal fixation member set comprising:
an internal fixation member including an internal fixation member body and a head located on an end of the internal fixation member body;
an outer member having a first opening and a second opening, and rotatably retaining the head; and
an inner member being inside the outer member and nearer the first opening than the head, the inner member being movable between a first position farther from the head and a second position nearer the second opening than the first position,
wherein the inner member includes a first interference part configured to interfere with the head,
the head includes a second interference part configured to interfere with the first interference part of the inner member,
the head has a first rotation range with the inner member at the first position and a second rotation range with the inner member at the second position, and the second rotation range is smaller than the first rotation range with an interference between the first interference part and the second interference part, and
the head has a reference rotational position at which the head is insertable into or extractable from the outer member, and the reference rotational position is included in the first rotation range and is not included in the second rotation range, wherein
the head further includes
a first semispherical part and a second semispherical part conforming to an imaginary spherical surface of the head, and
a flat belt between the first semispherical part and the second semispherical part and along the imaginary spherical surface, and
the head is insertable into and extractable from the outer member through the second opening at the reference rotational position with the flat belt being oriented along an edge of the second opening of the outer member.

12. The internal fixation member set according to claim 11, further comprising:
a C-shaped member having an outer peripheral surface conforming to the imaginary spherical surface of the head, the C-shaped member being configured to fit in the flat belt.

13. An internal fixation member retainable by an outer member being tubular and having a first opening and a second opening and by an inner member movable between a first position and a second position inside the outer member, the internal fixation member comprising:
an internal fixation member body placeable in a bone; and
a head joined to one end of the internal fixation member body, the head being retainable nearer the second opening than the inner member inside the outer member,
wherein with the head at a reference rotational position with respect to the outer member, the head is insertable into and extractable from the outer member,
the inner member includes a first interference part configured to interfere with the head, the head includes a second interference part configured to interfere with the first interference part of the inner member, the head has a first rotation range with the inner member at the first position and a second rotation range with the inner member at the second position, and the second rotation range is smaller than the first rotation range with an interference between the first interference part and the second interference part, the reference rotational position at which the head is inserted into or extracted from the outer member is included in the first rotation range and is not included in the second rotation range, the internal fixation member body includes a screw shaft, and the second interference part has an engagement hole engageable with a tool for turning the screw shaft.

14. The internal fixation member according to claim 13, wherein the internal fixation member body includes a screw shaft, a hook, or a pin.

\* \* \* \* \*